(12) United States Patent
Bowers et al.

(10) Patent No.: US 8,536,120 B2
(45) Date of Patent: Sep. 17, 2013

(54) GHRELIN/GROWTH HORMONE RELEASING PEPTIDE/GROWTH HORMONE SECRETATOGUE RECEPTOR ANTAGONISTS AND USES THEREOF

(75) Inventors: Cyril Y. Bowers, New Orleans, LA (US); Gloria S. Tannenbaum, Hampstead (CA); David H. Coy, New Orleans, LA (US); Simon J. Hocart, New Orleans, LA (US)

(73) Assignee: The Administrators of The Tulane Educational Fund, New Orleans, LA (US)

( * ) Notice: Subject to any disclaimer, the term of this patent is extended or adjusted under 35 U.S.C. 154(b) by 524 days.

(21) Appl. No.: 12/298,826

(22) PCT Filed: Apr. 30, 2007

(86) PCT No.: PCT/US2007/010389
§ 371 (c)(1), (2), (4) Date: Oct. 28, 2008

(87) PCT Pub. No.: WO2007/127457
PCT Pub. Date: Nov. 8, 2007

(65) Prior Publication Data
US 2009/0069245 A1    Mar. 12, 2009

Related U.S. Application Data

(60) Provisional application No. 60/795,960, filed on Apr. 28, 2006.

(51) Int. Cl.
| | |
|---|---|
| *A61K 31/15* | (2006.01) |
| *A61K 31/216* | (2006.01) |
| *A61K 38/08* | (2006.01) |
| *C07K 7/06* | (2006.01) |

(52) U.S. Cl.
USPC ............ 514/4.8; 514/5.3; 514/6.9; 514/21.8; 514/510; 514/640; 530/329; 560/45; 564/256

(58) Field of Classification Search
None
See application file for complete search history.

(56) References Cited

U.S. PATENT DOCUMENTS

| 4,880,778 A | * | 11/1989 | Bowers et al. | 514/11.3 |
| 5,234,906 A | * | 8/1993 | Young et al. | 514/6.8 |

(Continued)

FOREIGN PATENT DOCUMENTS

| EP | 1541171 A | 6/2005 |
| WO | 00/29011 A | 5/2000 |

(Continued)

OTHER PUBLICATIONS

Schioth et al. Characterization of the binding of MSH-B . . . Neuropeptides. 1997, vol. 31, pp. 565-571.*

(Continued)

*Primary Examiner* — Jeffrey E Russel
(74) *Attorney, Agent, or Firm* — Ronald I. Eisenstein; Nixon Peabody LLP

(57) ABSTRACT

The present invention provides novel compounds that have been demonstrated to be modulators of the ghrelin receptor (growth hormone secretagogue receptor, GHS-R1a and subtypes, iso forms and variants thereof). These compounds are useful as antagonists of the ghrelin receptor as well as inverse agonist, partial agonist or a combination of these activities as medicaments for treatment and prevention of a range of medical conditions including, but not limited to, metabolic and/or endocrine disorders, gastrointestinal disorders, cardiovascular disorders, obesity and obesity-associated disorders, diabetes, central nervous system disorders, genetic disorders, and hyperproliferative disorders.

10 Claims, 10 Drawing Sheets

(56) References Cited

U.S. PATENT DOCUMENTS

| | | | |
|---|---|---|---|
| 5,767,085 A * | 6/1998 | Johansen et al. | 514/11.3 |
| 5,932,548 A | 8/1999 | Deghenghi | |
| 6,124,263 A * | 9/2000 | Muccioli et al. | 514/11.2 |
| 2002/0128322 A1* | 9/2002 | Scammell et al. | 514/618 |
| 2003/0195144 A1* | 10/2003 | Svendsen et al. | 514/8 |
| 2005/0148515 A1* | 7/2005 | Dong | 514/17 |
| 2007/0060527 A1* | 3/2007 | Fogelman et al. | 514/18 |

FOREIGN PATENT DOCUMENTS

| | | | |
|---|---|---|---|
| WO | 2005/039625 A | 5/2005 | |
| WO | 2007/095347 A | 8/2007 | |

OTHER PUBLICATIONS

Bednarek et al., J Med Chem., 43:4370-6 (2000). "Structure-Function Studies on the New Growth Hormone-Releasing Peptide, Ghrelin: Minimal Sequence of Ghrelin Necessary for Activation of Growth Hormone Secretagogue Receptor 1a."
Bitar et al., Biochem Biophy Res Comm 180(1):156-161 (1991). "Effects of Substance P/Bombesin Antagonists on the Release of Growth Hormone by GHRP and GHRH."
Bodart et al., Circ. Res., 90:844-849 (2002). "CD36 Mediates the Cardiovascular Action of Growth Hormone-Releasing Peptides in the Heart."
Bowers, C.Y., Handbook of Physiology, Section 7, The Endocrine System, vol. V: Hormonal Control of Growth, Chapter 10 (Oxford University Press, NY), pp. 267-297 (1999). "Growth Hormone Releasing Peptides (GHRPs)."
Bowers, C.Y., J Clin Endocrinol Metab, 86:1464-1469 (2001). "Unnatural Growth Hormone-Releasing Peptide Begets Natural Ghrelin."
Bowers, C.Y., Endocrinology, 146 (6):2508-9 (2005). "Octanoyl Ghrelin is Hypothalamic Rooted."
Bowers et al., In: Fat Loss, Wasting and Cachexia in Medicine, (Ed) Schuster M and Mantovani G, Springer Verlag, Chapter 5.7, p. 219-234 (2006). "Biochemistry of the Growth Hormone-Releasing Peptides, Secretagogues and Ghrelin."
Bowers et al., Contemporary Endocrinology: Energy Metabolism and Obesity: Research and Clinical Applications, pp. 125-154 (2007). "The Role of Growth Hormone Secretagogues and Ghrelin in Feeding and Body Composition."
Camina, J.P., Journal of Neuroendocrinology, 18:65-76 (2006). "Cell Biology of the Ghrelin Receptor."
Gelling, R.W. et al., Endocrinology, 145(10):4575-4582 (2004). "Effect of Uncontrolled Diabetes on Plasma Ghrelin Concentrations and Ghrelin-Induced Feeding."
Holst et al., Molecular Endocrinology, 17(11):2201-2210 (2003). "High Constitutive Signaling of the Ghrelin Receptor—Identification of a Potent Inverse Agonist."
Holst et al., The Journal of Biological Chemistry, 279(51):53806-53817 (2004). "Common Structural Basis for Constitutive Activity of the Ghrelin Receptor Family."
Holst et al., The Journal of Biological Chemistry, 282(21):15799-15811 (2007). "Identification of an Efficacy Switch Region in the Ghrelin Receptor Responsible for Interchange between Agonism and Inverse Agonism."
Inui et al., FASEB J., 18:439-456 (2004). "Ghrelin, Appetite, and Gastric Motility: The Emerging Role of the Stomach as an Endocrine Organ."
Kojima et al., Nature, 402:656-660 (1999). "Ghrelin is a Growth-Hormone-Releasing Acylated Peptide from Stomach."
Korbonits et al., Frontiers in Neuroendocrinology, 25:27-68 (2004). "Ghrelin—A Hormone with Multiple Functions."
Laferrere et al., The Journal of Clinical Endocrinology & Metabolism, 90(2):611-614 (2005). "Growth Hormone Releasing Peptide-2 (GHRP-2), Like Ghrelin, Increases Food Intake in Healthy Men."
Laferrere et al., Obesity, 14:1056-1063 (2006). "Obese Subjects Respond to the Stimulatory Effect of the Ghrelin Agonist Growth Hormone-Releasing Peptide-2 on Food Intake."
Nakazato et al., Nature, 409:194-198 (2001). "A Role for Ghrelin in the Central Regulation of Feeding."
Sethumadhavan et al., Biochemical and Biophysical Research Communications, 178(1):31-37 (1991). "Demonstration and Characterization of the Specific Binding of Growth Hormone-Releasing Peptide to Rat Anterior Pituitary and Hypothalamic Membranes."
Tannenbaum et al., In: Brain Somatic Cross-Talk and the Central Control of Metabolism, Springer-Verlag Berlin Heidelberg, pp. 65-80 (2002). "Ghrelin and the Growth Hormone Neuroendocrine Axis."
Tannenbaum et al., Endocrinology, 144(3):967-974 (2003). "Interrelationship Between the Novel Peptide Ghrelin and Somatostatin/Growth Hormone-Releasing Hormone in Regulation of Pulsatile Growth Hormone Secretion."
Tschop et al., Nature, 407:908-913 (2000). "Ghrelin Induces Adiposity in Rodents."
Van Der Lely et al., Endocrine Reviews, 25(3):426-457 (2004). "Biological, Physiological, Pathophysiological, and Pharmacological Aspects of Ghrelin."
Veeraragavan et al., Life Sciences, 50:1149-1155 (1992). "Growth Hormone-Releasing Peptide (GHRP) Binding to Porcine Anterior Pituitary and Hypothalamic Membranes."
Wortley et al., The Journal of Clinical Investigation, 115(12):3573-3578 (2005). "Absence of Ghrelin Protects Against Early-Onset Obesity."
Wren et al., The Journal of Clinical Endocrinology & Metabolism, 86(12):5992-5995 (2001). "Ghrelin Enhances Appetite and Increases Food Intake in Humans."
Zigman et al., The Journal of Clinical Investigation, 115(12):3564-3572 (2005). "Mice Lacking Ghrelin Receptors Resist the Development of Diet-Induced Obesity."
Zigman et al., The Journal of Comparative Neurology, 494:528-548 (2006). "Expression of Ghrelin Receptor mRNA in the Rat and the Mouse Brain."
Asakawa, A, et al., Gut, 52:947-952 (2003). "Antagonism of ghrelin receptor reduces food intake and body weight gain in mice."
Beck, B. et al., Life Sciences, 76(4):473-478 (2004). "Feeding response to ghrelin agonist and antagonist in lean and obese Zucker rats."
Kundu, B. et al., Protein and Peptide Letters, 5(2):83-86 (1998). "Wound healing activity of peptides related to growth hormone releasing hexapeptide."
Momany, F.A. et al., Endocrinology, 108(1):31-39 (1981). "Design, synthesis, and biological activity of peptides which release growth hormone in vitro."
Sawyer, T.K. et al., Peptide Research, 2(1):140-146 (1989). "Discovery and structure-activity relationships of novel alpha-melanocyte-stimulating hormone inhibitors."
Veeraragavan, K. et al., Life Sciences, 50(16):1149-1155 (1992). "Growth hormone-releasing peptide (GHRP) binding to porcine anterior pituitary and hypothalamic membranes."

* cited by examiner

GHRELIN/GROWTH HORMONE RELEASING PEPTIDE/GROWTH HORMONE SECRETATOGUE RECEPTOR ANTAGONISTS AND USES THEREOF

CROSS-REFERENCE TO RELATED APPLICATIONS

This application is a 35 U.S.C. 371 National Stage of International Application No. PCT/US2007/010389 filed on Apr. 30, 2007, which designates the United States, and which claims the benefit under 35 U.S.C. §119(e) of U.S. Provisional Application No. 60/795,960 filed on Apr. 28, 2006, the entire contents of which are incorporated herein by reference.

FIELD OF THE INVENTION

This invention relates to novel compounds that disrupt the activity of ghrelin, growth hormone releasing peptide and the growth hormone secretagogue, receptor when introduced to animals, preferably humans, and methods of use thereof.

BACKGROUND OF THE INVENTION

The elevation of growth hormone (GH) levels in animals, e.g., mammals including humans, upon administration of GH-releasing compounds can lead to enhanced body weight. Ghrelin, identified as an endogenous ligand for the GH secretagogue receptor (GHS-R) is a powerful stimulator of pulsatile GH secretion and exhibits intricate interactions with the primary hypothalamic GH regulators (1-3). Ghrelin as well as growth hormone releasing peptides (GHRPs) and growth hormone secretagogues (GHSs) also function as potent orexigenic peptides (4-7). Initial peptide antagonists that inhibited the binding activity of GHSs in hypothalamic tissue in vitro were reported in 1991-92 (8-10). This included the Substance P analog, [$Arg^1$ $DPhe^5$ $DTrp^{7,9}$ $Leu^{11}$]-Substance P, that subsequently was demonstrated by Hoist et al (vide infra) to have both inverse agonist and ghrelin-R antagonist activity. Orexigenic compounds stimulate appetite.

Ghrelin is a 28 amino acid peptide, which has a unique structure among peptide hormones as it is acylated at Ser3 usually with an n-octanyl moiety (Bednarek et al., 2000; Kojima et al., 1999). This post-translational modification is essential for the activity of the hormone—as mediated through the seven transmembrane 0 (7TMG) protein coupled ghrelin receptor—both in vitro and in vivo (Kojima et al., 1999; Nakazato et al., 2001; Tschop et al., 2000).

Plasma levels of ghrelin rise precipitously in the blood before meals, when the stomach is empty, and fall after or during food consumption. Since intracardiac venous (i.v.) or intracerebroventricular (i.c.v) administration of ghrelin increases food intake, it appears that the physiological role of ghrelin is a link or messenger between the stomach and the hypothalamus and the pituitary. One hypothesis is that when an organism is getting ready for a meal, the CNS sends signals to the GI tract telling that a meal is about to be consumed in order to obtain information back about the status of the digestive process, state of distension etc. from the various chemical and mechanical sensors in the gut. Here, ghrelin could be an important hormonal messenger, which is sent back to the central nervous system (CNS) as a signal telling that there is no food in the stomach and that the gastrointestinal (GI) tract is ready for a new meal. In such a paradigm it is clear that a blocker of the ghrelin receptor would be a very efficient anti-obesity agent, as it would block the meal initiating, appetite signal from the GI tract.

The ghrelin receptor, GHS-R1a, belongs to a relatively small family of 7 transmembrane G-protein coupled receptors (11). A number of findings demonstrate how the ghrelin receptor may uniquely play a role in mediating the action on GH release and food intake. This includes ghrelin receptor genetics, mutations, structure, intracellular signaling, high constitutive activity, enhancement of the number of hypothalamic ghrelin receptors during starvation, etc. A spectrum of growth and metabolic changes occur in mice as a result of knockout of the ghrelin molecule as well as the ghrelin receptor. Adiposity in mice followed overexpression of the ghrelin receptor in hypothalamic growth hormone releasing hormone (GHRH) arcuate neurons. Over time, select biological effects of ghrelin/GHSs, especially non-endocrine effects, have been revealed which presumably occur via subtypes receptors of ghrelin or perhaps ghrelin receptors with select mutations. Evidence indicates binding and activation of the multifunctional CD36 receptor by GHSs. Another noteworthy finding of the ghrelin receptor was that under pathophysiological conditions the density of this receptor was reported to be five times greater in atherosclerotic coronary arteries (12).

Holst and Schwartz characterized the high constitutive activity of this receptor. Also, they demonstrated inhibition of the constitutive activity of the [$DArg^1$, $DPhe^5$, $DTrp^{7,9}$ $Leu^{11}$]-substance P analog which has been previously characterized both in vitro and in vivo as a weak competitive receptor antagonist to acute and chronic actions of GHRP-2 and ghrelin. These investigators demonstrated in vitro that this analog has 2 types of ghrelin receptor inhibiting activities. At a low dose (5 nM, $IC_{50}$), this Sub P analog is a potent inverse receptor agonist since it decreases elevated intracellular IP3 levels in the absence of ghrelin but also it is a weak ghrelin GHRP-6 competitive receptor antagonist since high dosages (630 nM, $IC_{50}$) inhibit receptor binding of both peptides (13, 14). Petersen, Holst, Schwartz et. al. reported that continuous i.c.v 7 day infusion of a very low dose of the Sub P ghrelin receptor inverse agonist inhibited body weight gain of male rats (15). This was a dose that would be too low to function as a competitive ghrelin receptor antagonist and thus it was considered to be due to the inverse agonist activity of the Sub P analog. In vitro evidence supports GHS-R antagonists with only inverse agonist or only ghrelin/GHS-R activity or a combination of the two (16).

Another possible novel functional role of the high constitutive activity of the ghrelin receptor in the CNS was proposed by Zigman et al on the distribution and functional implication of the ghrelin receptor in the brain of the rat and mouse (17). They proposed that the high constitutive activity of the ghrelin receptor plays a key functional role at CNS sites at which the receptor is expressed within the blood brain barrier and thus does not have immediate access to circulating ghrelin. This is in contrast to the ghrelin receptor located in the arcuate nucleus and dorsal vagal complex role. Thus it is possible that select GHSs, because of their different chemistry, may have ready access to brain sites inaccessible to ghrelin. If this occurs, GHSs' actions at these sites may alter the CNS ghrelin constitutive activity via receptor number and/or activity.

Although regulation of food intake by numerous hormones reveals its complexity, the inhibition of ghrelin induced food intake implies a fundamental biological functional aspect of the ghrelin system. For example, in the absence of the ghrelin receptor, transgenic female and male mice fed a high fat diet eat less food, less of the consumed calories are stored, fat is more of the energy substrate, and body weight and body fat are less in these mice than control mice (17, 18). When the ghrelin receptor was absent and mice were fed a normal diet, body weight and body fat were decreased in female but not in male mice. In the absence of the ghrelin peptide, transgenic male mice (female mice not studied) had less rapid body weight gain on a high fat diet (19). This was associated with increased energy expenditure and increased locomotive activity as well as decreased adiposity. Both of these studies indicate the ghrelin system is involved in body weight control especially when consuming a high caloric type of obese inducing diet. In the absence of the ghrelin receptor (GHS-R1a), ghrelin no longer increased food intake. Thus, the singularity of this receptor for mediating ghrelin induced food intake is indicated. Also, hyperphagia is an established risk factor in diabetes mellitus in humans and evidence indicates that sub-threshold doses of ghrelin increases food intake in streptozotocin treated rats (20). Experimental studies in rats revealed interrelationships of ghrelin, somatostatin and GHRH on function of the GH axis (21, 22).

Thus, compounds which effectively inhibit the ghrelin receptor are needed to disrupt the activity of ghrelin at the level of the CNS. Such compounds would be useful in the treatment of metabolic diseases and disorders such as obesity, diabetes mellitus, and inhibition of growth hormone secreted from tumors such as pituitary, prostate, osteoblast, pancreatic and hepatoma. Relevant basic and clinical ghrelin and GHS data have been discussed by Bowers et al (23, 24) as well as by other investigators (25-27).

SUMMARY OF THE INVENTION

We have surprisingly discovered new groups of compounds that provide desirable in vitro and in vivo inhibition of activation of the ghrelin receptor, GHS-R1a.

In one embodiment, the compounds have the formula: $A_1$-$A_2$-$A_3$-$A_4$-$A_5$-$A_6$ (Formula I), wherein $A_1$ is His, Tyr, desamino Tyr, D or LAla, β-Ala, CyclohexylAla (Cyclohexylalanine), DArg, Ava (aminovaleric acid), Gly, <Glu (pyroglutamic acid), αAib (alpha-aminoisobutyric acid), γAbu (gamma-aminobutyric acid), αAbu (alpha-aminobutyric acid), α,γAbu (alpha, gamma-diaminobutyric acid or 2,4-diaminobutyric acid), DVal, DPhe, DThr, DPal (pyridylalanine), DLys, AcDLys, DLeu, DTrp, Dβnaphthylalanine, or AcDβnaphthylalanine. There can be a normal or reduced psi (ψ, $CH_2NH$) peptide bond between the positions 1 and 2. Alternatively, $A_1$ may be amino acids with methylation of the terminal nitrogen of the alpha carbon atom of the $A_1$ residue when a terminal nitrogen is present at the α carbon atom; and $A_2$ is Dαnaphthylalanine, Dβnaphthylalanine, D or L Trp, D or L Phe, Ala, His, PicLys (N$^ε$-picoloyl-lysine), or DCyclohexylalanine, wherein $A_2$ is with or without methylation of the terminal nitrogen of the α carbon atom of the $A_2$ residue. In one embodiment, $A_2$ could have extended aromatic chains, such as, for example, D-4-halo-Phe, D-4-pyrolidylalanine, homologues and analogues thereof, wherein $A_2$ is with or without methylation of the terminal nitrogen of the α carbon atom of the $A_2$ residue;
$A_3$ is D or L Lys, lysine derivatives, Arg, arginine derivatives, Orn, Phe, Trp, Leu, Pro, Ala, Ser, Pal, or α,γAbu;
$A_4$ is D or L Trp, Phe, Ala, Ser, Tyr, Met, Pro, Thr, ILys, or CyclohexylAla;
$A_5$ is D or L Trp, Phe, Ala, Lys, Arg, Orn, Thr, Leu, or DCyclohexylAla; and
$A_6$ is Lys, Arg, Orn, D or L Phe, Pro, Nle (norleucine), or α,γAbu; or prodrugs, metabolite or pharmaceutically acceptable salts thereof, wherein the $A_6$ residue can be present either in a C terminal amidated form or as a free carboxylic acid.

In one preferred embodiment, the ghrelin receptor antagonist is HisDβNalDLysTrpDPheLysNH$_2$, or analogues, prodrug, metabolite, or pharmaceutical salts thereof.

In another embodiment, the ghrelin receptor antagonist is HisDTrpDLysTrpDPheLys NH$_2$.

In another embodiment, the compounds of the formulas $A_1$-$A_2$-$A_3$-$A_4$-$A_5$-$A_6$ excludes HisDβNalDLysTrpDPheLysNH$_2$.

In one embodiment, the compounds have the formula: $A_7$-$A_8$-$A_9$-$A_{10}$ (Formula II), wherein $A_7$ is DαNal, DβNal, AcDβNal, AcDαNal, Tyr, AcDTyr, Lys, D Phe, His, αAbu α,γAbu, γAbu, DcyclohexylAla, or isonipecotic carboxylic acid (inip);
$A_8$ is D or L Trp, Ala, His, Phe, or Leu;
$A_9$ is D or L Trp, Ala, CyclohexylAla, Phe, Pro, Lys, or Sarcosine (N-methylglycine) (Sar), or a free acid carboxyl group;
$A_{10}$ is D or L Arg, Phe, CyclohexylAla, Lys, Ser, or NMePhe (methylated phenylalanine amino nitrogen), DPal, Aib, or Orn.

In one embodiment, the compounds have the formula:

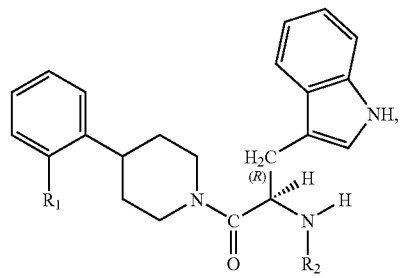

Formula III wherein $R_1$ is a hydroxyl group (—OH); and $R_2$ is —H,

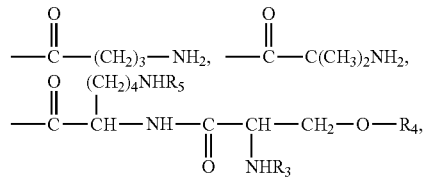

or isomers thereof.
$R_3$ is —H,

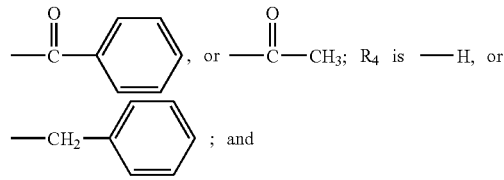

; $R_4$ is —H, or

; and $R_5$ is —H, or

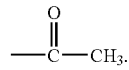

In one embodiment, the compounds have the formula:

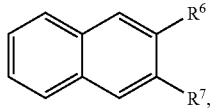

Formula IV wherein $R_6$ is

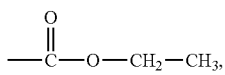

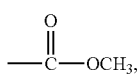

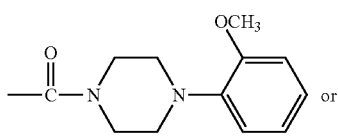

or

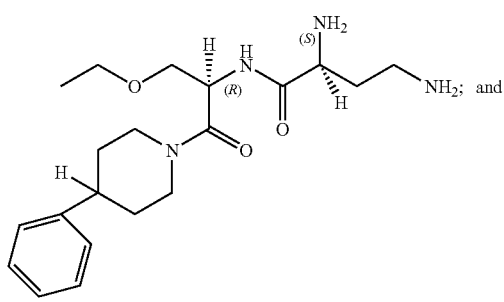

$R_7$ is —H,

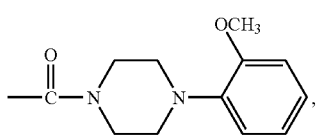

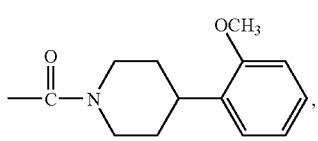

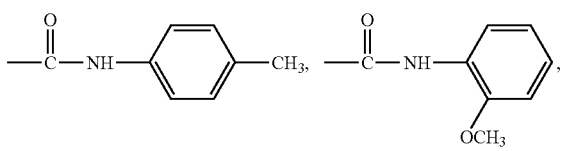

or isomers thereof.

In one embodiment, the compounds have the formula

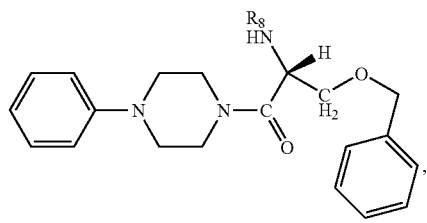

Formula V wherein $R_8$ is —H,

or isomers thereof.

Such compounds can be administered to a mammal, e.g. a human, to disrupt the activity of ghrelin at the level of the CNS. Thus, the present invention provides novel compounds and methods for their use in disrupting ghrelin. Accordingly, methods for the treatment of various diseases and disorders such as obesity, overeating, diabetes, unregulated cellular proliferation, and cancer using the novel compounds of the present invention are encompassed.

We have shown that administration of such compounds attenuates GH pulses and reduces food intake in mammals. Thus, in one embodiment, methods for the treatment of obesity are encompassed. In this method, an individual, preferably an obese or overweight individual, is administered a compound of Formula I of the present invention such as HisDβNalDLysTrpDPheLysNH$_2$, analogues, prodrug, metabolite, or pharmaceutical salts thereof. The compound may also be administered in combination with other anti-obesity compounds. Such compounds are well known in the art.

Typically, an overweigh individual is considered to have a body mass index (BMI) of over 25 but under 30 and an obese individual is considered to have a BMI of over 30.

The methods and uses of the present invention are applicable for both sexes and all age groups including children and teenagers.

Also encompassed is a method for the treatment of obesity related diseases and disorders such as, but not limited to diabetes mellitus, metabolic syndrome, hypertension, elevated plasma insulin concentrations, insulin resistance, dyslipidemias, and hyperlipidemia, by administering to the individual in need thereof an effective ghrelin activity inhibiting amount of the novel compounds of the present invention.

In another embodiment, the invention provides a method for reducing a desire of a human subject to consume calories following gastric banding or gastric bypass surgery, by administering the ghrelin receptor antagonists of the present invention.

The present invention also provides methods for treating hormonally functional endocrine or non-endocrine tumors, such as, pituitary tumors, including ACTH-secreting pituitary tumors, in a mammal. The inventive methods involve administering to the mammal having or at risk for developing a pituitary tumor a therapeutically effective amount of the novel ghrelin receptor antagonist of the present invention. In one embodiment, the ghrelin receptor antagonist is administered in combination with other compounds useful in the treatment of pituitary tumor such as, for example, PPARγ ligands. Such PPARγ ligands include thiazolidinediones (TZDs), such as troglitazone, pioglitazone, and rosiglitazone.

In another embodiment, methods for the treatment of tumors that produce prolactin are encompassed. In this method, the novel ghrelin receptor antagonists of the present invention are administered to an individual with or at risk for developing a tumor that produces prolactin. Such tumors include, but are not limited to, breast and prostate cancer.

The novel ghrelin receptor antagonists of the present invention may also be used to inhibit adrenocorticotropic hormone. Also encompassed are methods for the treatment of ectopic neuroendocrine tumors such as functional ectopic neuroendocrine tumors, carcinoid and pancreatic tumors via the administration of ghrelin receptor antagonists.

The novel ghrelin receptor antagonists may also function to inhibit signaling via subtype receptors of ghrelin in addition to GHS-type 1 receptors. Thus, methods to treat diseases and disorders associated with these subtype receptors, e.g. prostate cancer, osteoblast cancer, pancreatic cancer, adenocarcinomas and hepatoma cells is encompassed in the present invention.

DETAILED DESCRIPTION OF THE INVENTION

Figure 1A:
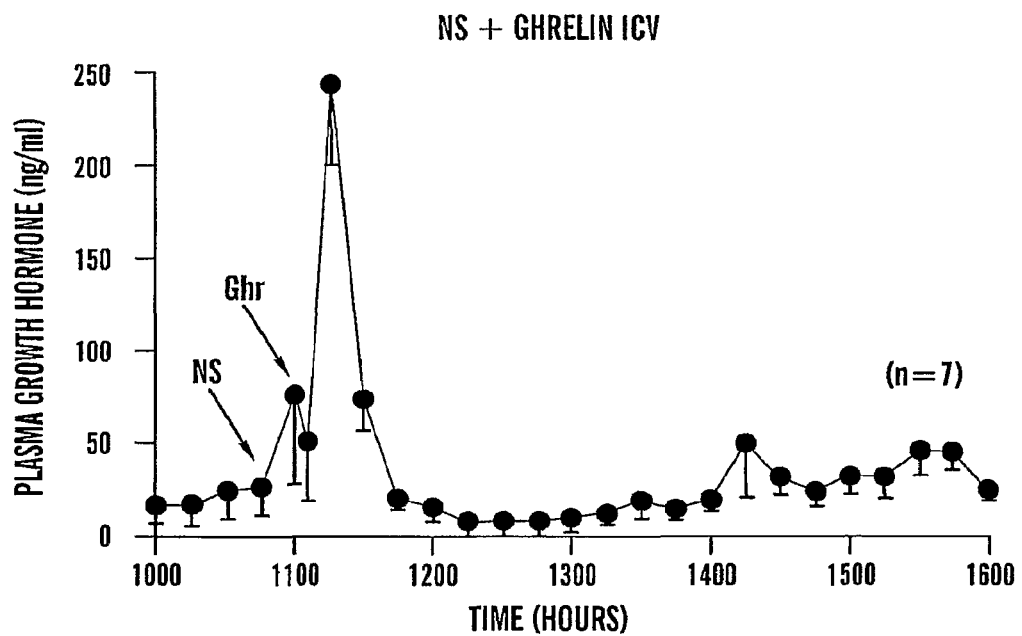
FIGS. 1A and 1B show mean plasma GH responses to 500 ng ghrelin administered icv 15 min after the icv injection of 5 μg GHS-A (FIG. 1B) or normal saline (FIG. 1A). Central pretreatment with GHS-A abolished the stimulatory action of ghrelin on GH release compared with normal saline i.c.v. pretreated controls. Values are the mean±SE. The number of animals in each group is shown in parentheses. Arrows indicate the times of i.c.v. injections.
Figure 1B:
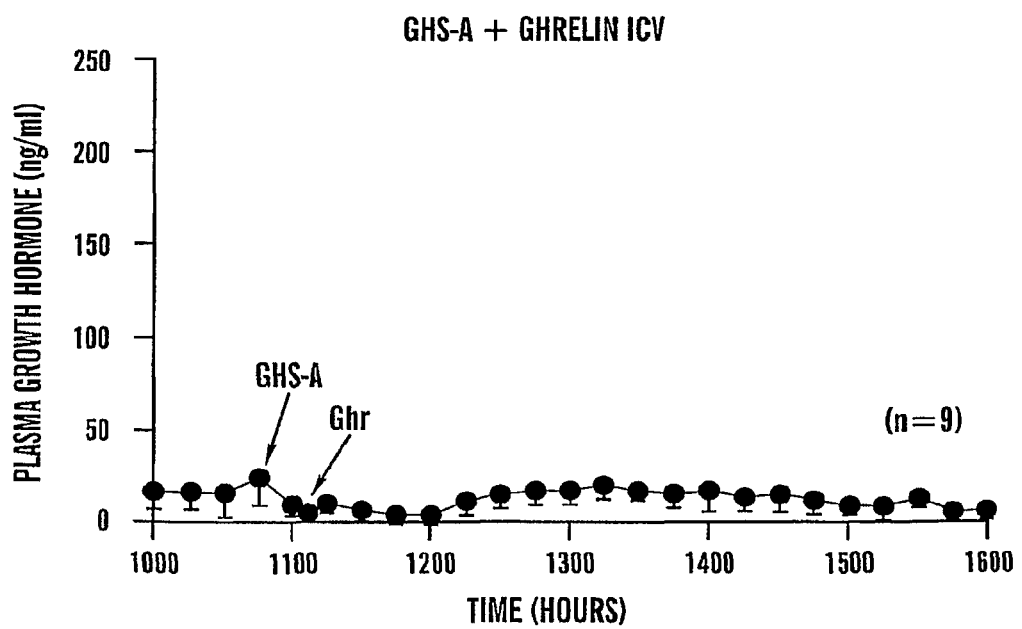
Figure 2A:
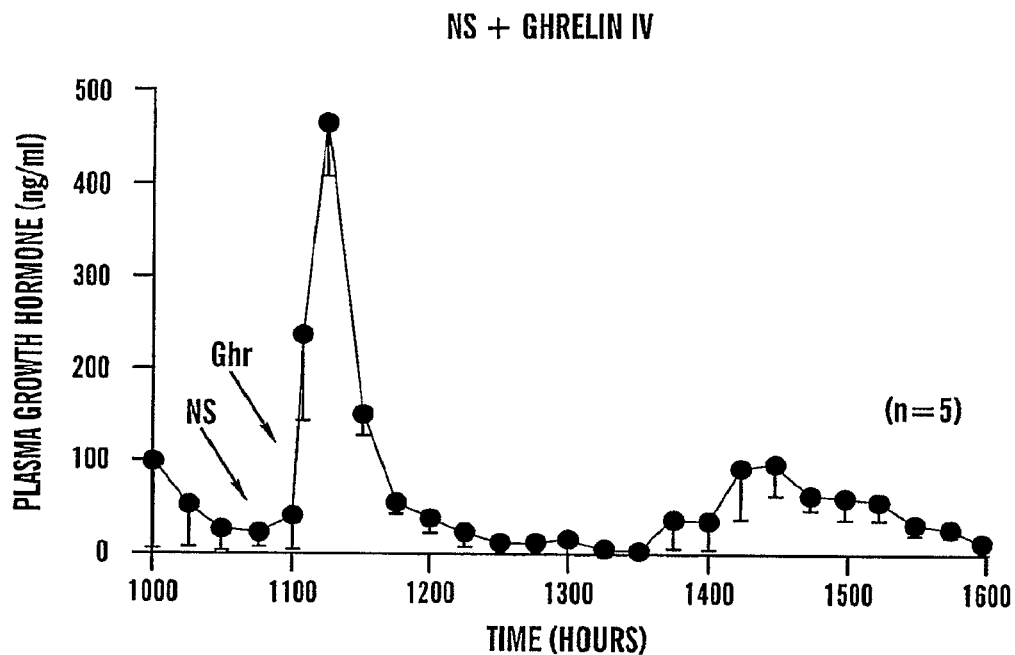
FIGS. 2A and 2B show mean plasma GH responses to 5 μg ghrelin administered iv 15 min after the iv injection of 250 μg GHS-A (FIG. 2B) or normal saline (FIG. 2A). Peripheral administration of GHS-A strongly blocked ghrelin's ability to release GH compared with normal saline-pretreated controls. Values are the mean±SE. The number of animals in each group is shown in parentheses. Arrows indicate the times of i.v. injections.
Figure 2B:
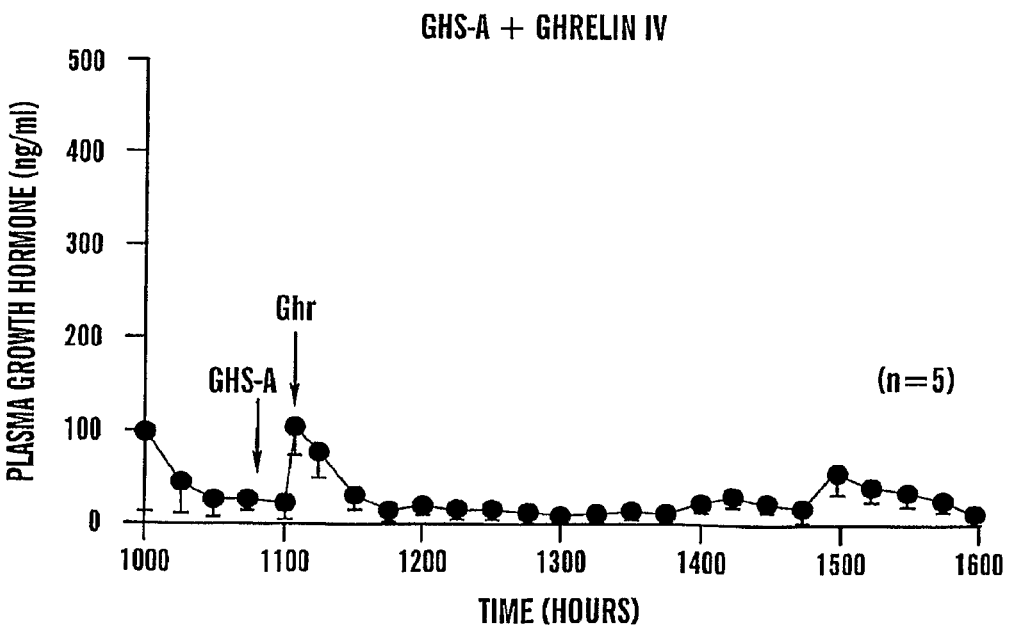
Figure 3:
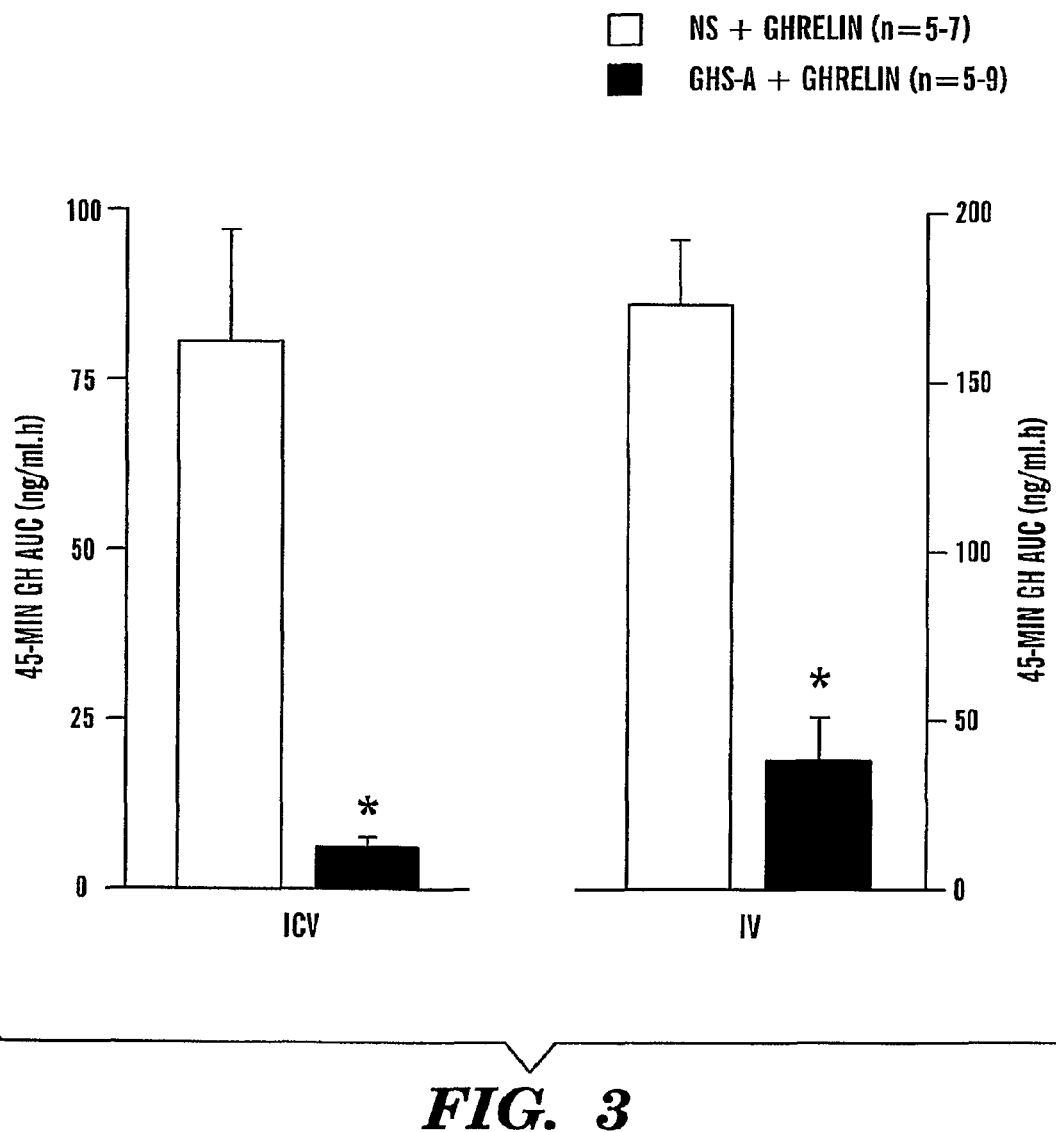
FIG. 3 shows a summary of the effects of GHS-A, given centrally (icv) or peripherally (iv), on ghrelin-induced GH release. The GH AUC following i.c.v. (500 ng) and i.v. (5 μg) ghrelin injection was reduced by 15- and 5-fold, respectively, in the GHS-A pretreated groups compared with their respective normal saline-treated controls. Each bar represents the mean±SE. *, P<0.0003 or less compared with normal saline-pretreated animals.
Figure 4A:
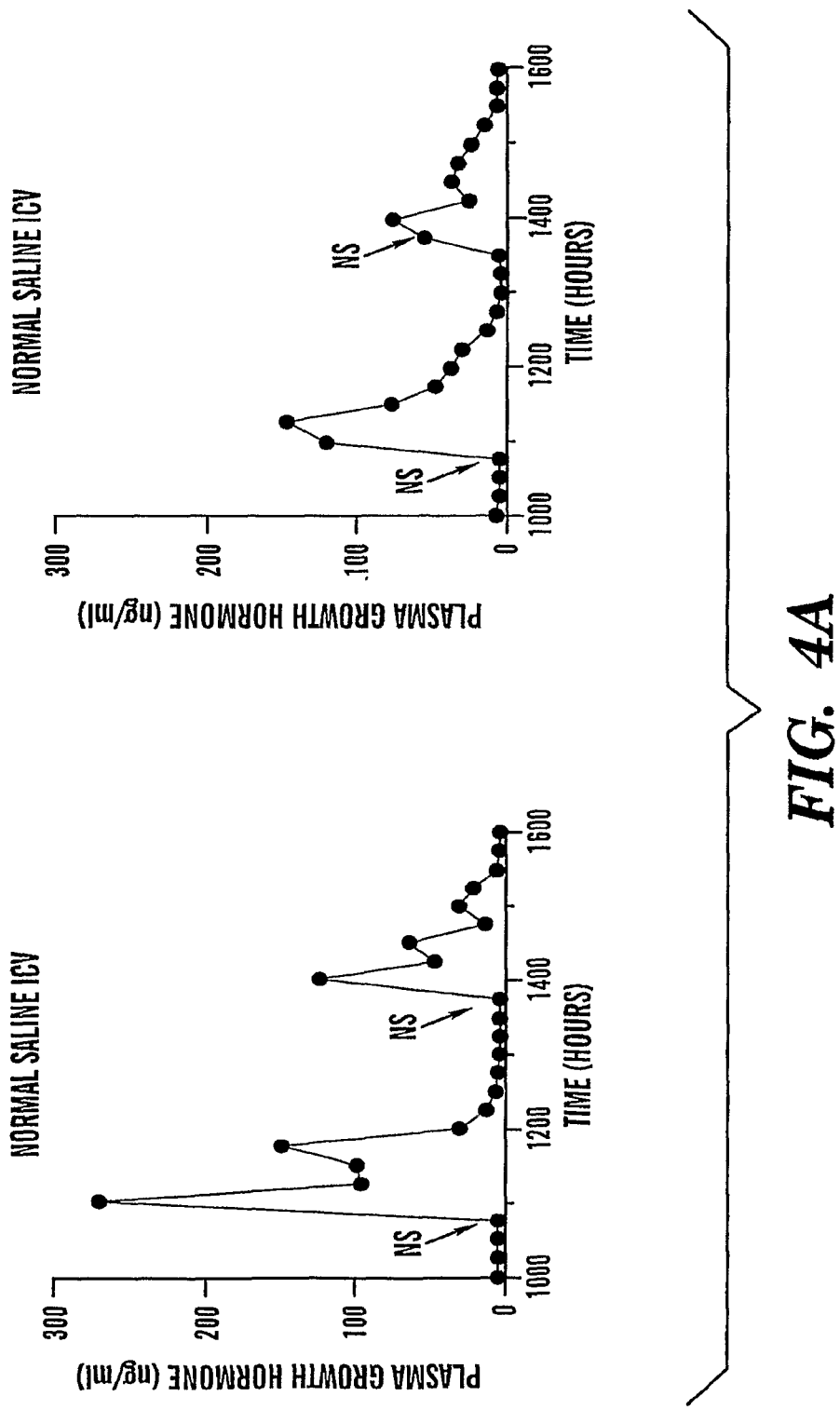
FIGS. 4A and 4B show that Individual representative plasma GH profiles in rats i.c.v. administered either 5 μg GHS-A (FIG. 4B) or normal saline (FIG. 4A) 15 min prior to the expected onset of the spontaneous GH secretory bursts typical of the male rat. GHS-A administration severely attenuated the amplitude of the spontaneous GH pulses compared with normal saline icv-injected controls. Arrows indicate the times of i.c.v. injections.
Figure 4B:
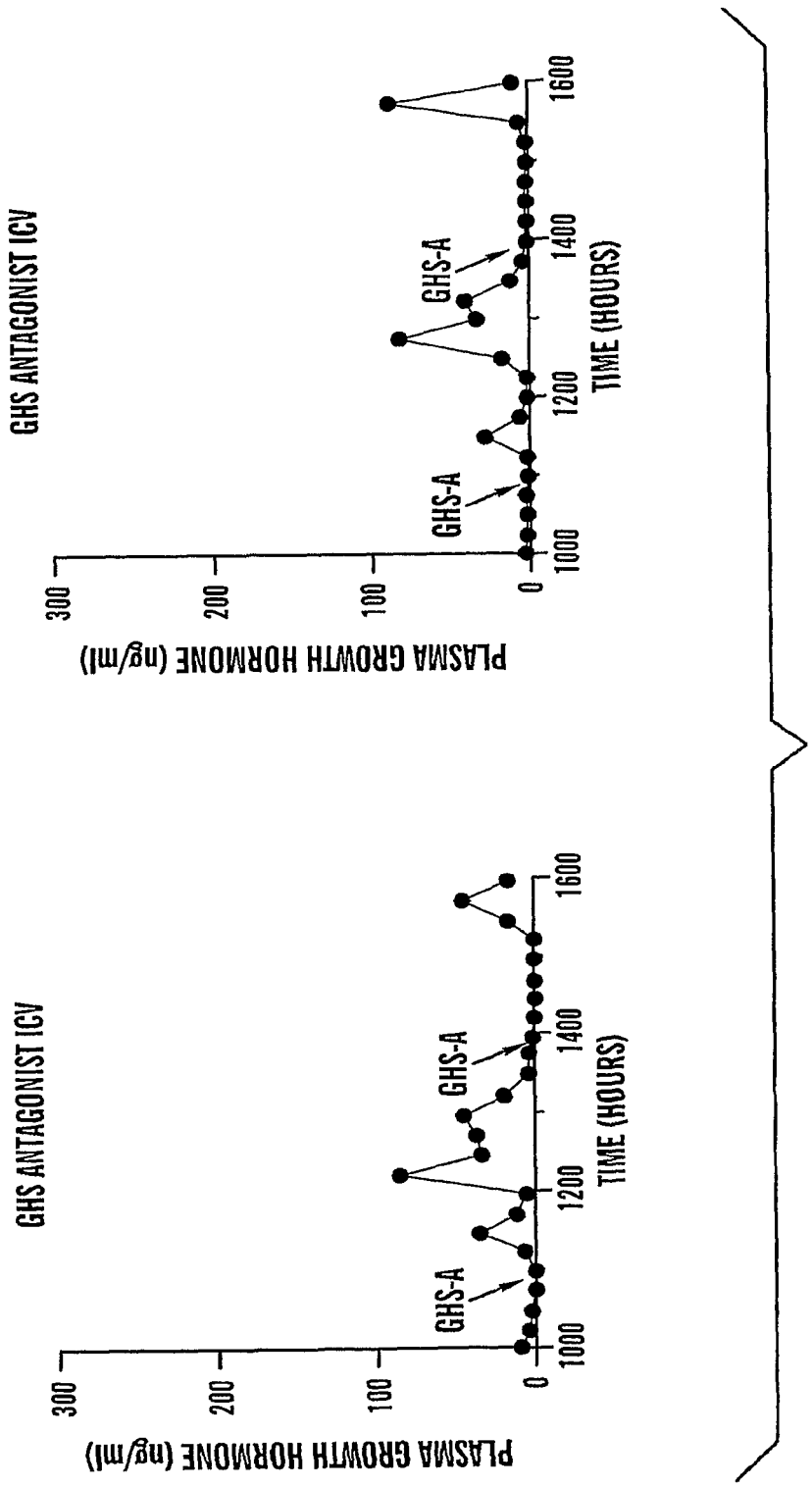
Figure 5:
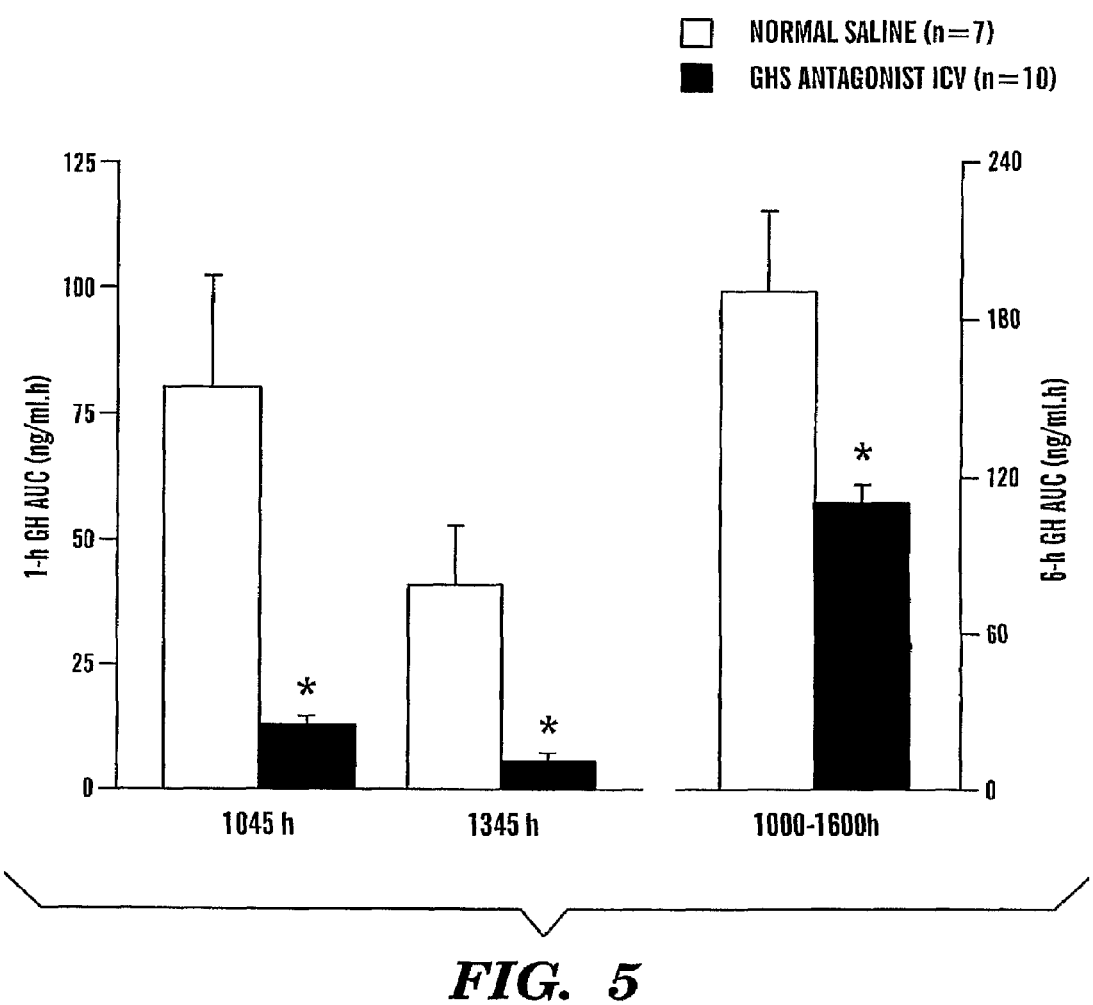
FIG. 5 shows that the 1-h GH AUC's of the spontaneous GH secretory episodes at 1100 h and 1400 h, and the overall 6-h GH AUC, were significantly reduced in animals treated i.c.v. with 5 μg GHS-A compared with normal saline i.c.v.-treated controls. Values are the mean±SE. *, P<0.01 or less compared with normal saline i.c.v.-treated group.
Figure 6:
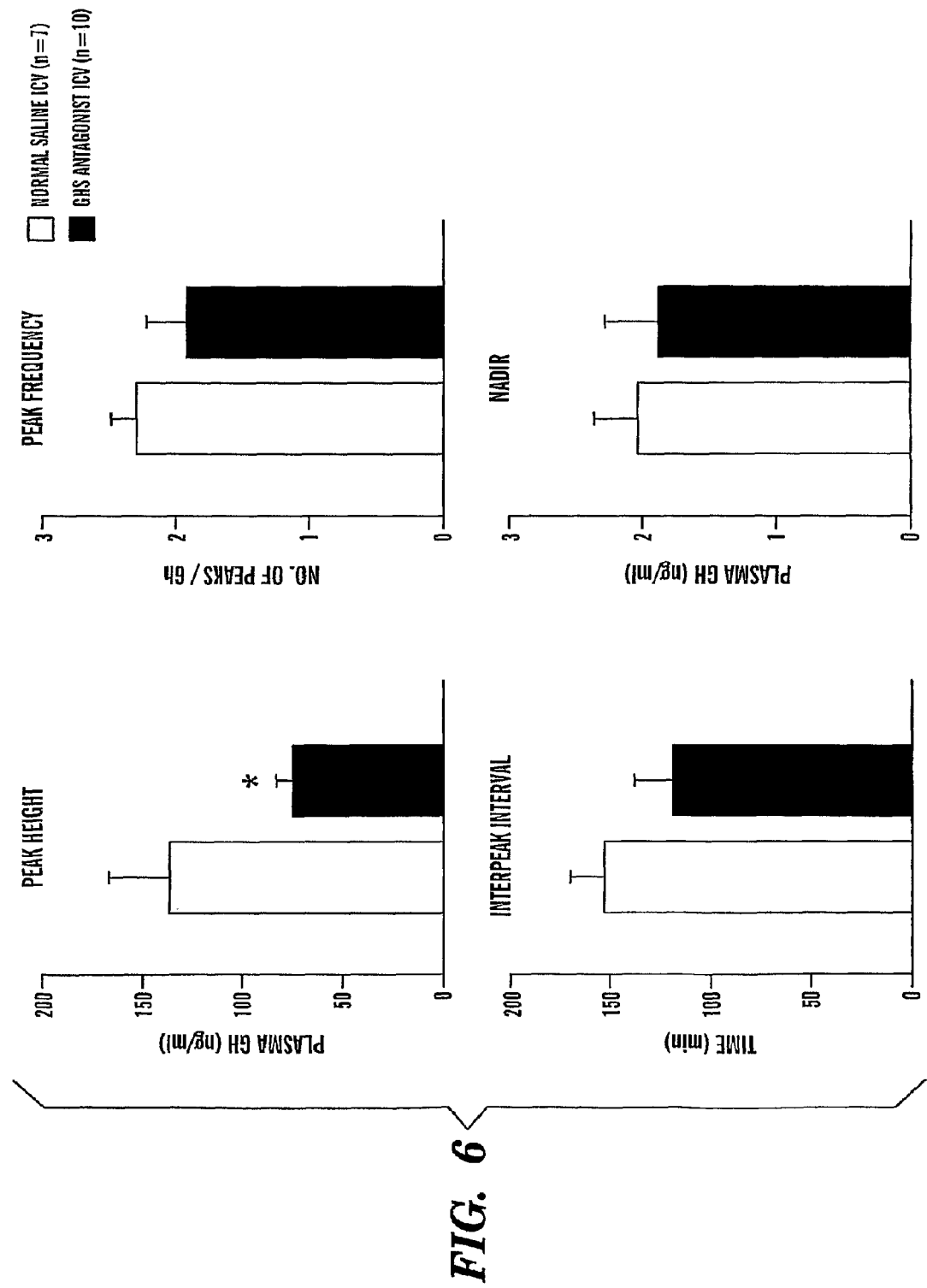
FIG. 6 shows a cluster analysis of the effects of centrally-administered GHS-A (5 μg) or normal saline on spontaneous GH pulse parameters. Cluster analysis revealed a significant suppression of GH peak height, but no significant effect of GHS-A on any other parameters of GH pulsatility, including GH peak frequency, interpeak interval and nadir, compared with normal saline icv-treated controls. Values are the mean±SE. *, P<0.03 vs. normal saline i.c.v.-treated controls.
Figure 7A:
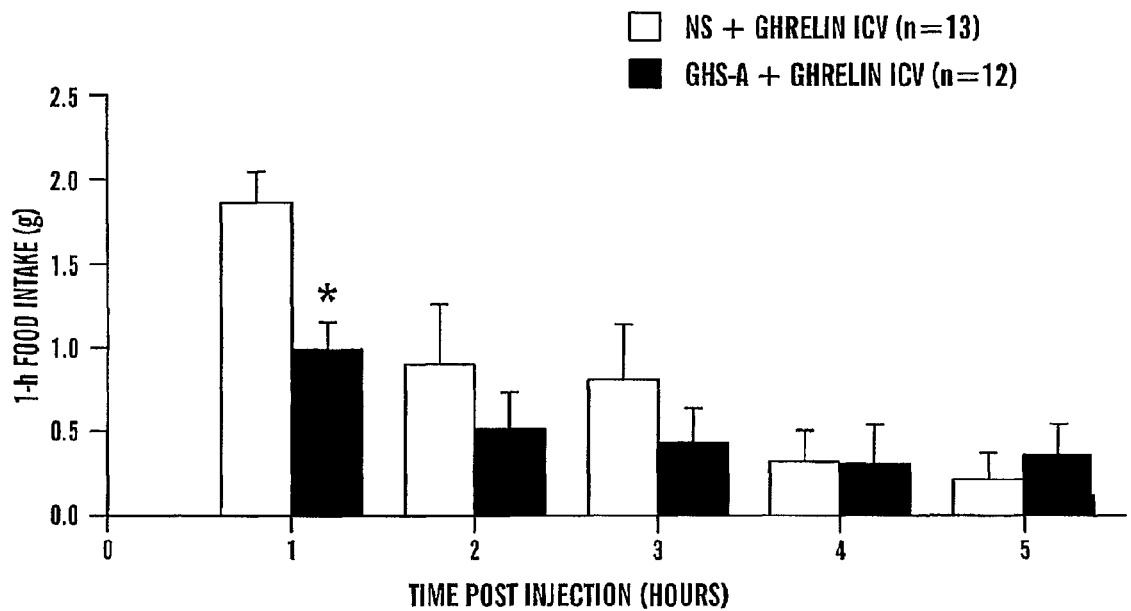
FIGS. 7A and 7B show a feeding response to icv-administered ghrelin (500 ng) in animals pretreated icv with either GHS-A (5 μg) or normal saline (FIG. 7A). GHS-A significantly inhibited ghrelin's stimulatory effects on food intake in the first hour after injections, compared with normal saline i.c.v.-pretreated controls (FIG. 7B). Cumulative food intake was significantly suppressed for up to 5 h after GHS-A injection. Values are the mean±SE. *, P<0.02 or less compared with normal saline icv-pretreated controls.
Figure 7B:
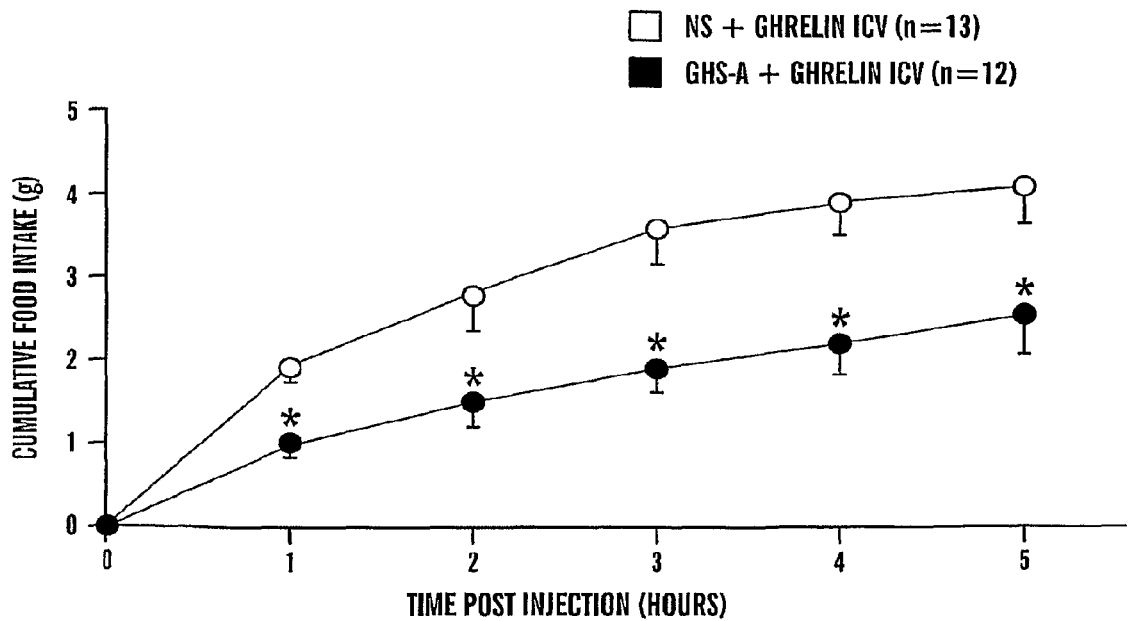
Figure 8A:
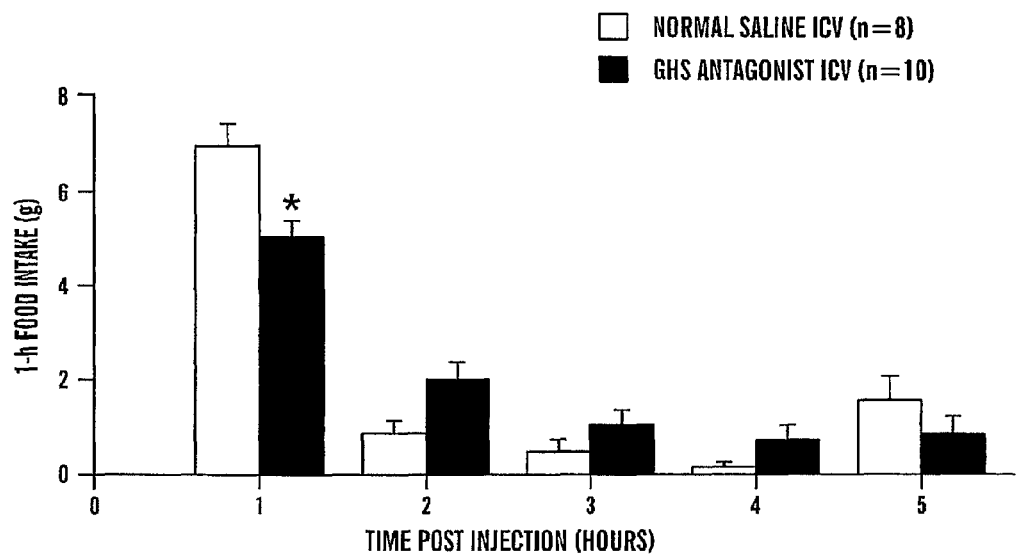
FIGS. 8A and 8B show the effects of icv-administered GHS-A (5 μg) or normal saline on spontaneous food intake in overnight-fasted animals (FIG. 8A). GHS-A significantly inhibited spontaneous food intake in the first hour after injection, compared with normal saline icv-treated controls (FIG. 8B). Cumulative food intake was not inhibited by GHS-A beyond the first hour after injection. Values are the mean±SE. *, P<0.004 compared with normal saline icv-treated controls.
Figure 8B:
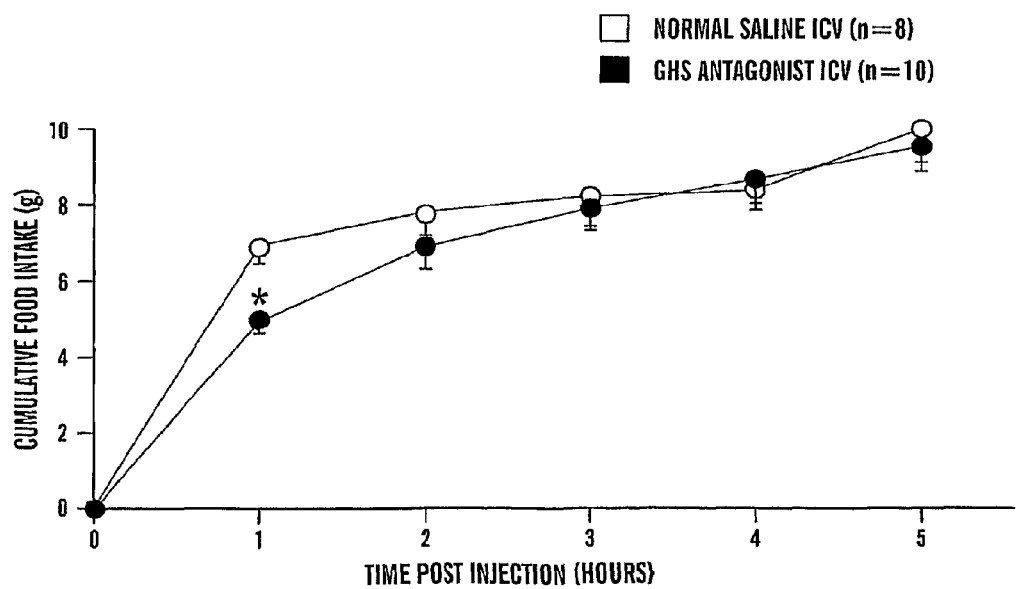
Figure 9:
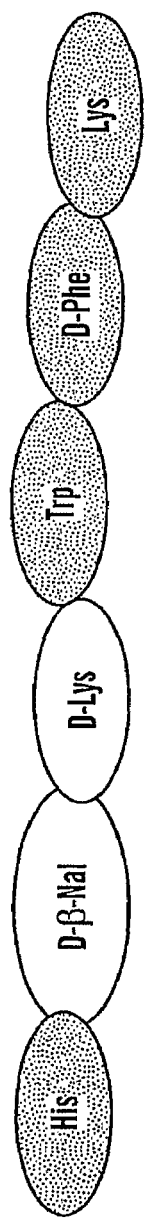
FIG. 9 shows a diagram of one ghrelin receptor antagonist HisDβNalDLysTrpDPheLysNH$_2$.

The present invention provides novel ghrelin, growth hormone releasing peptide and the growth hormone secretagogue receptor antagonists.

Compounds

In one embodiment, the ghrelin receptor antagonist has the formula: $A_1$-$A_2$-$A_3$-$A_4$-$A_5$-$A_6$ (Formula I) as described more fully above. One preferred antagonist has the formula His-DβNalDLysTrpDPheLysNH$_2$.

In one embodiment, the ghrelin receptor antagonist is His-DTrpDLysTrpDPheLysNH$_2$.

In another embodiment, the antagonist is HisDTrpDArgTrpDPhe NH$_2$.

In yet another embodiment, the antagonist is HisDTrpDLysTrpDPhe NH$_2$.

Examples of ghrelin receptor antagonists are shown in Tables 1-12. Examples of some preferred compounds are listed below.

TyrDTrpDLysTrpDPheNH2
TyrDTrpLysTrpDPhe NH2
HisDTrpDLysTrpDPheNH2
HisDTrpDLysPhe DTrpNH2
HisDTrpDArgTrpDPheNH2
HisDTrpDLysTrpDPheLysNH2
DesaminoTyrDTrpAlaTrpDPheNH2
DesaminoTyrDTrpDLysTrpDPheNH2
DeaminoTyrDTrpSerTrpDPheLysNH2
DesaminoTyrDTrpSerTrpDPheNH2
HisDTrpDTrpPheMetNH2
TyrDTrpDTrpPhePheNH2
GlypsiDβNalAlaTrpDPheLysNH2
GlypsiDβNalDLysTrpDPheLysNH2
Dala DβNalDLysDTrpPheLysNH2
HisDβNalDLysTrpDPheLysNH2
AlaHisDTrpDLysTrpDPheLysNH2

TABLE 1

In Vitro Ghrelin/GHRP/GHS Receptor Antagonist Activity on Stimulated GH (ng/ml) release from isolated pituitary glands by the pituitary incubation method. Stimulator is His-DTrp-Ala-Trp-DPhe-Lys-NH$_2$ at 10 ng/ml

| Peptide Antagonist | Control | Stimulated Control | Peptide Antagonist Dosage μg/ml | | | | | | |
|---|---|---|---|---|---|---|---|---|---|
| | | | 0.1 | 0.3 | 1 | 3 | 10 | 30 | 100 |
| 1-Tyr-DTrp-DLys-Trp-DPhe-NH$_2$ | 47 ± 22 | 1528 ± 214 | | | | −480 ± 95 | | −363 ± 66 | |
| 2-Tyr-DTrp-Lys-Trp-DPhe-NH$_2$ | −461 ± 163 | 1053 ± 182 | | | | | | | −555 ± 121 |
| 3-His-DTrp-DLys-Trp-DPhe-NH$_2$ | 57 ± 77 | 2120 ± 311 | | 1765 ± 160 | | 949 ± 178 | | 91 ± 103 | |
| 4-His-DTrp-DLys-Phe-DTrp-NH$_2$ | N/A | | | | | | | | |
| 5-His-DTrp-DArg-Trp-DPhe-NH$_2$ | −461 ± 163 | 1953 ± 182 | | | | 341 ± 222 | −125 ± 101 | −122 ± 44 | |
| 6-His-DTrp-DLys-Trp-DPhe-Lys-NH$_2$ | −129 ± 52 | 1267 ± 64 | | 952 ± 200 | 324 ± 181 | 134 ± 91 | −83 ± 132 | −175 ± 59 | |
| 7-DesaminoTyr-DTrp-Ala-Trp-DPhe-NH$_2$ | 58 ± 77 | 2120 ± 311 | | | | 1302 ± 269 | | −959 ± 75 | |
| 8-DesminoTyr-DTrp-DLys-Trp-DPhe-NH$_2$ | 223 ± 203 | 5189 ± 1513 | 4297 ± 1061 | 2404 ± 802 | 688 ± 327 | −466 ± 432 | −1068 ± 318 | −576 ± 110 | |
| 9-DeaminoTyr-DTrp-Ser-Trp-DPhe-Lys-NH$_2$ | 8 ± 305 | 4436 ± 1006 | | | | | 3325 ± 391 | 3810 ± 621 | |
| 10-DesaminoTyr-DTrp-Ser-Trp-DPhe-NH$_2$ | 8 ± 305 | 4436 ± 1006 | | | | | 3119 ± 488 | 3258 ± 682 | |
| 11-His-DTrp-DTrp-Phe-Met-NH$_2$ | −129 ± 52 | 1267 ± 164 | | 1542 ± 523 | 323 ± 69 | 445 ± 188 | 287 ± 68 | −319 ± 95 | |
| 12-Tyr-DTrp-DTrp-Phe-Phe-NH$_2$ | 47 ± 22 | 1528 ± 214 | | 1274 ± 329 | | | 1034 ± 182 | −167 ± 157 | |

TABLE 2

In Vivo Ghrelin/GHRP/GHS Receptor Antagonist Activity on Stimulated GH (ng/ml) release from rat. Sitmulator is DAla-DβNal-Ala-Trp-DPhe-Lys-NH2 at 0.3 μg or 1 μg

| Peptide Antagonist | Control | Stimulated Control 0.3 μg | Stimulated Control 1 μg | Peptide Antagonist Dosage μg/i.v. | | | | |
|---|---|---|---|---|---|---|---|---|
| | | | | 1 | 3 | 10 | 30 | 100 |
| 1-Glyψ[CH$_2$NH]-DβNal-Ala-Trp-DPhe-Lys-NH$_2$ | 138 ± 11 | 1412 ± 400 | | | | 1112 ± 200 | 578 ± 82 | |
| | 138 ± 11 | | 3214 ± 276 | | | 2307 ± 176 | 890 ± 236 | |
| | 164 ± 14 | | 3105 ± 429 | | | 1842 ± 454 | 1135 ± 140 | |
| 2-Glyψ[CH$_2$NH]-DβNal-DLys-Trp-DPhe-Lys-NH$_2$ | 143 ± 19 | | 2406 ± 288 | 2305 ± 320 | 1990 ± 196 | 1550 ± 284 | 946 ± 133 | 462 ± 122 |
| 3-DAla-DβNal-DLys-DTrp-Phe-Lys-NH$_2$ | 327 ± 39 | | 4950 ± 98 | | | | 2884 ± 828 | 1198 ± 114 |
| 4-His-DβNal-DLys-Trp-DPhe-Lys-NH$_2$ | 91 ± 46 | 2253 ± 252 | | | | | 733 ± 85 | |
| | 91 ± 46 | | 2825 ± 134 | | | | 1487 ± 397 | 818 ± 269 |
| 5-Ala-His-DTrp-DLys-Trp-DPhe-Lys-NH$_2$ | 91 ± 46 | 2253 ± 252 | | | | | 1487 ± 397 | |
| 6-Alaψ[CH$_2$NH]-DβNal-Ala-Trp-DPhe-Lys-NH$_2$ | 164 ± 14 | | 3104 ± 429 | | 2771 ± 157 | 2341 ± 416 | 1948 ± 450 | 1639 ± 221 |

TABLE 3

In Vivo Ghrelin/GHRP/GHS Receptor Antagonist Activity on Unstimulated Basal GH (ng/ml) Release from rat.

| Partial Agonist/Antagonist Peptide | Control | Stimulated Control 0.3 μg | Stimulated Control 1 μg | Peptide Dosage μg/i.v. | | | | |
|---|---|---|---|---|---|---|---|---|
| | | | | 1 | 3 | 10 | 30 | 100 |
| 1-DβNal-Ala-Trp-DPhe-Ala-NH₂ | 253 ± 34 | 1991 ± 214 | | 623 ± 60 | 694 ± 70 | 654 ± 58 | 713 ± 71 | |
| 2-DAla-DcyclohexylAla-Ala-Phe-DPhe-Nle-NH₂ | 204 ± 46 | 1850 ± 324 | | 435 ± 152 | 195 ± 34 | 250 ± 41 | 393 ± 51 | 697 ± 75 |
| 3-DcyclohexylAla-Ala-Phe-DTrp-Lys-NH₂ | 204 ± 46 | 1765 ± 330 | | 199 ± 63 | 266 ± 68 | 199 ± 23 | 346 ± 82 | 350 ± 61 |
| 4-DAla-DβNal-Ala-Thr-DThr-Lys-NH₂ | 244 ± 56 | 1538 ± 215 | | | 255 ± 38 | | 288 ± 31 | 386 ± 57 |
| 5-DcyclohexylAla-Ala-Trp-DPhe-NH₂ | 176 ± 44 | 2282 ± 258 | | | 181 ± 28 | 237 ± 18 | 354 ± 81 | 771 ± 76 |
| 6-DAla-DβNal-Ala-Ala-DAla-Lys-NH₂ | 135 ± 19 | 1485 ± 200 | | | 235 ± 43 | 178 ± 33 | 172 ± 15 | 185 ± 39 |
| 7-DβNal-Ala-Trp-DPhe-Leu-NH₂ | 145 ± 48 | 1470 ± 338 | | | 253 ± 79 | 277 ± 43 | 347 ± 66 | 645 ± 117 |
| 8-His-DTrp-Phe-Trp-DPhe-Lys-NH₂ | 240 ± 55 | | 2766 ± 726 | 67 ± 14 | 141 ± 53 | 197 ± 70 | 509 ± 48 | |
| 9-DAla-DβNal-DAla-DTrp-Phe-Lys-NH₂ | 100 ± 22 | | 4785 ± 798 | 184 ± 55 | 467 ± 201 | 244 ± 107 | | |
| 10-βAla-Trp-DAla-DTrp-Phe-NH₂ | 195 ± 33 | | 4130 ± 349 | | | | 341 ± 46 | 636 ± 171 |
| 11-His-Trp-DAla-DTrp-Phe-LysNH₂ | 150 ± 26 | 1847 ± 362 | | 204 ± 44 | 127 ± 44 | 83 ± 5 | | |

TABLE 4

In Vivo Ghrelin/GHRP/GHS Receptor Antagonist Activity on Unstimulated and Stimulated (S) GH (ng/ml) release from rats.
The Stimulator is DAla-DβNal-Ala-Trp-DPhe-Lys-NH2 at 0.3 μg, 1 μg, or 10 μg.

| Peptide Antagonist (P) | | Control | Stimulated Control 0.3 | Stimulated Control 1 | Peptide Antagonist Dosage μg/i.v. | | | | |
|---|---|---|---|---|---|---|---|---|---|
| | | | | | 1 | 3 | 10 | 30 | 100 |
| Pentobarbital Rats | | | | | | | | | |
| 1-DLys-DβNal-Ala-Trp-DPhe-Lys-NH₂ | −S | 197 ± 81 | | | | 616 ± 169 | 847 ± 17 | 629 ± 148 | 228 ± 45 |
| 1-DLys-DβNal-Ala-Trp-DPhe-Lys-NH₂ | P + S | | 5052 ± 511 | | | 5232 ± 346 | 3404 ± 396 | 704 ± 169 | |
| 2-DAla-DβNal-DLys-DTrp-Phe-Lys-NH₂ | −S | 327 ± 39 | | | | | | 323 ± 50 | 812 ± 6 |
| 2-DAla-DβNal-DLys-DTrp-Phe-Lys-NH₂ | P + S | | | 4950 ± 98 | | | | 2884 ± 828 | 1198 ± 114 |
| Non-Pentobarbital Rats | | | | 10 μg | | | | | |
| 1-Tyr-DAla-Phe-Aib-NH₂ | −S | 12 ± 1 | | | | | | 18 ± 1 | |
| 1-Tyr-DAla-Phe-Aib-NH₂ | P + S | | | 72 ± 9 | | | | 23 ± 5 | |
| 2-Tyr-DAla-Sar-NMePhe-NH₂ | −S | 12 ± 1 | | | | | | 18 ± 4 | |
| 2-Tyr-DAla-Sar-NMePhe-NH₂ | P + S | | | 72 ± 9 | | | | 24 ± 6 | |

TABLE 5

In Vivo Ghrelin/GHRP/GHS Receptor Antagonist Activity on Unstimulated Basal GH (ng/ml) release from rats.

| Peptide Antagonist | Control | Stimulated Control 0.3 μg | Stimulated Control 1 μg | Peptide Antagonist Dosage μg/i.v. | | | | |
|---|---|---|---|---|---|---|---|---|
| | | | | 1 | 3 | 10 | 30 | 100 |
| 1-αγAbu-DTrp-DTrp-Ser-NH₂ | 106 ± 9 | | 2742 ± 206 | 80 ± 35 | | 62 ± 15 | 67 ± 8 | |
| 2-αγAbu-DTrp-DTrp-Lys-NH₂ | 136 ± 31 | | 1968 ± 294 | 57 ± 7 | 84 ± 18 | 62 ± 15 | | |
| 3-αγAbu-DTrp-DTrp-Orn-NH₂ | 167 ± 13 | | 2819 ± 530 | 118 ± 16 | | 126 ± 27 | 79 ± 31 | |
| 4-αAbu-DTrp-DTrp-Orn-NH₂ | 167 ± 13 | | 2819 ± 530 | 85 ± 25 | | 88 ± 18 | 50 ± 6 | |
| 5-DThr-DαNal-DTrp-DPro-Arg-NH₂ | 164 ± 23 | | 2691 ± 281 | 60 ± 5 | 130 ± 24 | 134 ± 31 | | |
| 6-DAla-Ala-DAla-DTrp-Phe-Lys-NH₂ | 180 ± 20 | | 4785 ± 798 | | | 228 ± 76 | 172 ± 14 | 153 ± 45 |
| 7-Alaψ[CH₂NH]His-DTrp-Ala-Trp-DPhe-Lys-NH₂ | 211 ± 30 | | 2335 ± 323 | 127 ± 32 | 147 ± 37 | | | |
| 8-Lys-DHis-DTrp-Phe-NH₂ | 211 ± 30 | | 2335 ± 323 | | | 121 ± 24 | | |
| 9-γAbu-DTrp-DTrp-Orn-NH₂ | 167 ± 13 | | 2819 ± 530 | 82 ± 28 | | 90 ± 5 | 113 ± 32 | |
| 10-inip-Trp-Trp-Phe-NH₂ | 155 ± 31 | | 2503 ± 240 | | | 69 ± 3 | 81 ± 10 | | inip = isonipecotic carboxylic acid
αγAbu = alpha gamma diaminobutyric acid

TABLE 6

In Vitro Ghrelin/GHRP/GHS Receptor Antagonist Activity on Unstimulated and Stimulated(S) GH (ng/ml) release from cell culture of pituitary cells. The Sitmulator is DAla-DβNal-Ala-Trp-DPhe-Lys-NH$_2$ at at 10 ng/ml.

| Peptide Antagonist (P) | | Control | Stimulated Control 10 ng/ml | Peptide Antagonist Dosage μg/ml | | | | | |
|---|---|---|---|---|---|---|---|---|---|
| | | | | 0.1 | 0.3 | 1 | 3 | 10 | 30 |
| 1-Ac-DTrp-Phe-DTrp-Leu-NH$_2$ | −S | 1640 ± 100 | | | | | | | 400 ± 20 |
| 1-Ac-DTrp-Phe-DTrp-Leu-NH$_2$ | P + S | | 2420 ± 0 | | | | 2100 ± 0 | 1200 ± 20 | 600 ± 20 |
| 2-Ac-DTrp-Phe-DTrp-Lys-NH$_2$ | −S | 1640 ± 100 | | | | | | | 350 ± 80 |
| 2-Ac-DTrp-Phe-DTrp-Lys-NH$_2$ | P + S | | 2420 ± 0 | | | | 1750 ± 10 | 800 ± 0 | 470 ± 30 |
| 3-Ac-DTrp-DTrp-Lys-NH$_2$ | −S | 1640 ± 100 | | | | | | 610 ± 30 | 420 ± 20 |
| 3-Ac-DTrp-DTrp-Lys-NH$_2$ | P + S | | 2420 ± 0 | | | | 1970 ± 70 | 1130 ± 30 | 900 ± 0 |
| 4-DLys-Tyr-DTrp-DTrp-Phe-Lys-NH$_2$ | −S | 1640 ± 100 | | | | | | 1340 ± 60 | 1060 ± 0 |
| 4-DLys-Tyr-DTrp-DTrp-Phe-Lys-NH$_2$ | P + S | | 2420 ± 0 | | | | 2100 ± 40 | 1710 ± 10 | 1270 ± 10 |
| 5-Ac-DβNal-Leu-Pro-NH$_2$ | −S | 1233 ± 49 | | | | | | | |
| 5-Ac-DβNal-Leu-Pro-NH$_2$ | P + S | | 2811 ± 229 | | | | 1998 ± 36 | 1206 ± 53 | 860 ± 33 |
| 6-βAla-Trp-DTrp-DTrp-Orn-NH$_2$ | −S | 1722 ± 205 | | | | | | | |
| 6-βAla-Trp-DTrp-DTrp-Orn-NH$_2$ | P + S | | 2385 ± 8 | | | 3103 ± 471 | | 1633 ± 34 | 1166 ± 13 |

TABLE 7

In Vitro Ghrelin/GHRP/GHS Receptor Antagonist Activity on Unstimulated and Stimulated (S) GH (ng/ml) release from cell culture of pituitary cells. The Stimulator is DAla-DβNal-Ala-Trp-DPhe-Lys-NH$_2$ at 1 ng/ml.

| Partial Agonist/Antagonist Peptide (P) | | Control | Stimulated Control 1 ng/ml | Peptide Dosage μg/ml | | | | |
|---|---|---|---|---|---|---|---|---|
| | | | | 1 | 3 | 10 | 30 | 100 |
| 1-DVal-DαNal-DTrp-Phe-Arg-NH$_2$ | −S | 480 ± 16 | | | 934 ± 34 | 850 ± 19 | 598 ± 7 | |
| 1-DVal-DαNal-DTrp-Phe-Arg-NH$_2$ | P + S | | 1399 ± 27 | | 949 ± 52 | 672 ± 64 | 520 ± 5 | |
| 2-DLeu-DαNal-DTrp-Phe-Arg-NH$_2$ | −S | 480 ± 16 | | | 1156 ± 10 | 971 ± 5 | 520 ± 5 | |
| 2-DLeu-DαNal-DTrp-Phe-Arg-NH$_2$ | P + S | | 1399 ± 27 | | 1136 ± 7 | 957 ± 44 | 777 ± 71 | |
| 3-CyclohexylLeu-DαNal-DTrp-Phe-Arg-NH$_2$ | P + S | 734 ± 6 | 1841 ± 41 | | 1362 ± 59 | 1021 ± 22 | | |
| 4-DTrp-DαNal-DTrp-Phe-Arg-NH$_2$ | P + S | 734 ± 6 | 1851 ± 41 | | 1239 ± 17 | 878 ± 28 | | |
| 5-DAla-DβNal-DPro-Arg-NH$_2$ | P + S | 734 ± 6 | 1851 ± 41 | | 1779 ± 27 | 1328 ± 59 | | |
| 6-Ac-DαNal-DTrp-Phe-Arg-NH$_2$ | −S | 480 ± 16 | | | 1106 ± 7 | 996 ± 16 | 704 ± 76 | |
| 6-Ac-DαNal-DTrp-Phe-Arg-NH$_2$ | P + S | | 1399 ± 27 | | 1128 ± 12 | 970 ± 25 | 704 ± 76 | |
| 7-DαNal-DTrp-Phe-Arg-NH$_2$ | −S | 480 ± 16 | | | 1170 ± 43 | 987 ± 52 | 727 ± 44 | |
| 7-DαNal-DTrp-Phe-Arg-NH$_2$ | P + S | | 1399 ± 27 | | 1288 ± 40 | 1079 ± 17 | 824 ± 29 | |
| 8-inip-Trp-Trp-Phe-NH$_2$ | −S | 625 ± 12 | | | | 553 ± 111 | 247 ± 9 | 132 ± 7 |
| 8-inip-Trp-Trp-Phe-NH$_2$ | P + S | | 749 ± 28 | | | 393 ± 6 | 278 ± 35 | 154 ± 4 | inip = isonipecotic carboxylic acid

TABLE 8

In Vitro Ghrelin/GHRP/GHS Receptor Antagonist Activity on Unstimulated Basal GH (ng/ml) release from cell cultures of pituitary cells.

| Peptide Antagonist (P) | Control | Stimulated control 1 ng/ml | Peptide Antagonist Dosage μg/ml | | | | |
|---|---|---|---|---|---|---|---|
| | | | 1 | 3 | 10 | 30 | 100 |
| 1-His-DTrp-DTrp-Lys-NH$_2$ | 1089 ± 47 | 1551 ± 2 | | 1124 ± 37 | 749 ± 10 | 615 ± 41 | |
| 2-Ac-DβNal-DTrp-NH$_2$ | 1089 ± 47 | 1551 ± 2 | | 1264 ± 2 | 980 ± 72 | 699 ± 7 | |
| 3-αAib-DTrp-DcyclohexylAla-NH$_2$ | 478 ± 8 | 1014 ± 8 | 980 ± 44 | 826 ± 32 | 602 ± 53 | 492 ± 11 | |
| 4-αAib-DTrp-DAla-cyclohexylAla-NH$_2$ | 478 ± 8 | 1014 ± 8 | 1086 ± 52 | 1103 ± 18 | 994 ± 22 | 704 ± 115 | |
| 5-DAla-DcyclohexylAla-Ala-Ala-Phe-DPhe-Nle-NH$_2$ | 500 ± 116 | 1991 ± 214 | 286 ± 75 | 177 ± 44 | 271 ± 38 | 376 ± 28 | |
| 6-DPhe-Ala-Phe-DPal-NH$_2$ | 176 ± 44 | | | 170 ± 19 | 181 ± 31 | 161 ± 20 | 146 ± 21 |
| 7-DPhe-Ala-Phe-DPhe-Lys-NH$_2$ | 368 ± 32 | | | | 267 ± 27 | 276 ± 65 | 360 ± 84 |
| 8-DLys-Tyr-DTrp-DTrp-Phe-NH$_2$ | 1403 ± 13 | | 1451 ± 19 | 1175 ± 77 | 1129 ± 6 | 744 ± 44 | |
| 9-Ac-DLys-Tyr-DTrp-DTrp-Phe-NH$_2$ | 1403 ± 13 | | | 105 ± 8 | 950 ± 91 | 782 ± 56 | 756 ± 1 |
| 10-Arg-DTrp-Leu-Tyr-Trp-Pro(cyclic Arg-Pro) | 1403 ± 13 | | | 1480 ± 19 | 802 ± 26 | 601 ± 16 | 509 ± 49 |
| 11-Ac-DβNal-PicLys-ILys-DPhe-NH$_2$ | 1333 ± 41 | | | 1013 ± 207 | 976 ± 13 | 928 ± 16 | |
| 12-DPal-Phe-DTrp-Phe-Met-NH$_2$ | 1333 ± 41 | | | 1081 ± 50 | 997 ± 30 | 425 ± 25 | |
| 13-DPhe-Trp-DPhe-Phe-Met-NH$_2$ | 1333 ± 41 | | | 1146 ± 34 | 1086 ± 32 | 871 ± 89 | |
| 14-DPal-Trp-DPhe-Phe-Met-NH$_2$ | 1333 ± 41 | | | 1105 ± 18 | 891 ± 4 | 567 ± 24 | |

ILys = Lys(iPr)

TABLE 9

In Vitro Ghrelin/GHRP/GHS Receptor Antagonist Activity on Unstimulated and Stimulated(S) GH (ng/ml) release from cell cultures of pituitary cells. The Stimulator is DAla-DβNal-Ala-Trp-DPhe-Lys-NH$_2$ at 1 ng/ml.

| Peptide Antagonist (P) | | Control | Stimulated control 1 ng/ml | Peptide Antagonist Dosage μg/ml | | | | |
|---|---|---|---|---|---|---|---|---|
| | | | | 1 | 3 | 10 | 30 | 100 |
| 1-βAla-Pal-DTrp-DTrp-Orn-NH$_2$ | −S | 894 ± 18 | | | | 759 ± 11 | 861 ± 25 | |
| | P + S | | 1232 ± 34 | | | 855 ± 11 | 828 ± 11 | |
| 2-αγAbu-Trp-DTrp-DTrp-Orn-NH$_2$ | −S | 894 ± 18 | | | | 609 ± 3 | 503 ± 5 | |
| | P + S | | 1232 ± 34 | | | 666 ± 2 | 578 ± 31 | |
| 3-βAla-Trp-DTrp-DTrp-Lys-NH$_2$ | −S | 894 ± 18 | | | | 733 ± 25 | 616 ± 21 | |
| | P + S | | 1232 ± 34 | | | 806 ± 45 | 596 ± 18 | |
| 4-γAbu-Trp-DTrp-DTrp-Orn-NH$_2$ | −S | 894 ± 18 | | | | 840 ± 30 | 634 ± 1 | |
| | P + S | | 1232 ± 34 | | | 835 ± 5 | 655 ± 40 | |
| 5-Ava-Trp-DTrp-DTrp-Orn-NH$_2$ | −S | 894 ± 18 | | | | 481 ± 3 | 406 ± 21 | |
| | P + S | | 1232 ± 34 | | | 505 ± 19 | 420 ± 34 | |

αγAbu = alpha gamma diaminobutyric acid

Ava = aminovaleric acid

TABLE 10

In Vitro Ghrelin/GHRP/GHS Receptor Antagonist Activity on Unstimulated and Stimulated(S) GH (ng/ml) release from cell cultures of pituitary cells. The Stimulator is DAla-DβNal-Ala-Trp-DPhe-Lys-NH$_2$ at 1 ng/ml.

| Partial Peptide/Non-peptide(P) | | Control | Stimulated Control 1 ng/ml | Partial Peptide/Non-peptide Dosage μg/ml | | | |
|---|---|---|---|---|---|---|---|
| | | | | 1 | 3 | 10 | 30 |
| 1-DTrp-4-phenylpiperdinamide | P + S | 385 ± 49 | 1060 ± 24 | 815 ± 26 | 390 ± 35 | 520 ± 61 | 577 ± 24 |
| | | | | 1085 ± 1 | 917 ± 4 | 344 ± 6 | 486 ± 29 |
| 2-2,3-di[N-(2-methoxylphenyl) piperazyl-naphthalene carboxylamide | P + S | 361 ± 30 | 905 ± 6 | 338 ± 3 | 204 ± 10 | 262 ± 4 | |
| | | | | 654 ± 18 | 442 ± 4 | 537 ± 28 | |
| | P + S | 385 ± 17 | 1153 ± 36 | | | 136 ± 11 | 118 ± 8 |
| | | | | | | 648 ± 16 | 309 ± 46 |
| 3-Benzamide-DSerDLysTrp-p-phenylpiperidinamide | P + S | 370 ± 24 | 1216 ± 26 | | 393 ± 54 | 369 ± 30 | |
| | | | | | 432 ± 25 | 353 ± 10 | |
| 4-Ser(Bzl)Lys(Ac)DTrp-p-phenylpiperidinamide | P + S | 385 ± 17 | 1153 ± 36 | | | 388 ± 41 | 273 ± 39 |
| | | | | | | 571 ± 32 | 399 ± 24 |
| 5-O-(2-methylallyl) benzophonone oxime | P + S | 969 ± 33 | 1461 ± 58 | | | 929 ± 28 | 616 ± 23 |
| | | | | | | 1281 ± 58 | 699 ± 53 |
| 6-D Ser(BZL)-N'-phenyl-N-piperazinamide | P + S | 626 ± 4 | 1016 ± 18 | | | 585 ± 10 | 368 ± 2 |
| | | | | | | 719 ± 26 | 435 ± 0 |
| 7-αAibDSer(BZL)-N'-phenyl-N-piperazinamide | P + S | 626 ± 4 | 1016 ± 18 | | | 777 ± 34 | 499 ± 18 |
| | | | | | | 878 ± 30 | 510 ± 15 |
| 8-2-[acetylester]-3-(p-m-methoxyl phenyl) piperidinamide]-naphthalene carboxamide | P + S | 421 ± 16 | 859 ± 4 | | | 373 ± 2 | 176 ± 11 |
| | | | | | | 480 ± 9 | 223 ± 22 |

TABLE 11

In Vitro Ghrelin/GHRP/GHS Receptor Antagonist Activity on Unstimulated and Stimulated(S) GH (ng/ml) release from cell cultures of pituitary cells. The Stimulator is DAla-DβNal-Ala-Trp-DPhe-Lys-NH$_2$ at 1 ng/ml.

| Partial Peptide/Non-peptide(P) | | Control | Stimulated Control 1 ng/ml | Partial Peptide/Non-peptide Dosage μg/ml | | | |
|---|---|---|---|---|---|---|---|
| | | | | 1 | 3 | 10 | 30 |
| 1-2-[methylester]-3-[p-methylphenylamide naphthalene carboxylamide | P + S | 626 ± 4 | 1016 ± 18 | | | 754 ± 32 | 498 ± 26 |
| | | | | | | 1149 ± 33 | 886 ± 29 |
| 2-p-phenyl(piperidinamide-DTrpLysSer(BZL)-acetylamide | P + S | 408 ± 40 | 905 ± 6 | 680 ± 13 | 489 ± 41 | 245 ± 16 | |
| 3-γAbuDTrp-p-[m-methoxyphenyl] piperidinamide | P + S | 364 ± 31 | 947 ± 11 | | | 557 ± 19 | 378 ± 18 |
| | | | | | | 526 ± 27 | 428 ± 22 |
| 4-αAibDTrp-p-(o-methoxylphenyl) piperidinamide | P + S | 377 ± 24 | 947 ± 33 | | | 365 ± 2 | 375 ± 30 |
| | | | | | | 441 ± 21 | 384 ± 16 |
| 5-2-[ethylester-3-m-methoxylphenylamide] naphthalene carboxylamide | P + S | 364 ± 31 | 947 ± 11 | | | 698 ± 18 | 552 ± 20 |
| | | | | | | 670 ± 32 | 458 ± 15 |
| 6-1,3-diaminobutyricamide-DβNal-4-phenylpiperidinamide | P + S | 626 ± 4 | 1016 ± 18 | | | 794 ± 34 | 504 ± 20 |
| | | | | | | 644 ± 33 | 529 ± 20 |

TABLE 12

In Vitro Ghrelin/GHRP/GHS Receptor Antagonist Activity on Unstimulated and Stimulated(S) GH (ng/ml) release from isolated pituitary glands by the pituitary incubation method. The Stimulator S = His-DTrp-Ala-Trp-DPhe-Lys-NH$_2$ (10 ng/ml) and Stimulator *S = Tyr-DTrp-Ala-Trp-Dphe-NH$_2$ (0.3 µg/ml)

| Peptide(P) | | Control | Stimulated Control | Peptide Dosage µg/ml | | | | |
|---|---|---|---|---|---|---|---|---|
| | | | | 1 | 3 | 10 | 30 | 100 |
| 1-His-DTrp-DLys-Trp-DPhe-NH$_2$ | P + S | 654 ± 255 | 8769 ± 583 | 8121 ± 687 | 5929 ± 857 | 3017 ± 413 | 269 ± 140 | |
| 2-Ala-His-DTrp-DLys-Trp-DPhe-Lys-NH$_2$ | P + S | 1674 ± 1171 | 5218 ± 507 | 4850 ± 539 | 947 ± 551 | 3977 ± 1360 | | |
| 3-DLys-Tyr-DTrp-Ala-Trp-DPhe-NH$_2$* | P + S | 148 ± 137 | 2218 ± 194 | | 1233 ± 268 | −2384 ± 868 688 ± 3233 | 916 ± 80 | |
| 4-His-DTrp-DArg-Trp-DPhe-NH$_2$ | P + S | −14 ± 62 | 776 ± 142 | | −109 ± 124 136 ± 108 | 209 ± 124 | −500 ± 104 −454 ± 95 | |
| 5-<Glu-His-Trp-DSer-DArg-NH$_2$ | | 246 ± 67 | | | | −4 ± 25 | 6 ± 34 | |
| 6-DPhe-DPhe-DTrp-Met-DLys-NH$_2$* | P + S | 148 ± 137 | 2218 ± 194 | | 1584 ± 136 | 1398 ± 98 | 1388 ± 300 | |

In another embodiment, the antagonist is a compound of Formula I other than HisDβNalDLysTrpDPheLysNH$_2$. Pharmaceutically acceptable organic and inorganic addition salts thereof are also included.

The abbreviations for the residues of amino acids used herein are in agreement with the standard nomenclature, and are as follows: L Gly—Glycine, L Tyr—Tyrosine, L Ile—Isoleucine, L Glu—Glutamic Acid, L Thr—Threonine, L Phe—Phenylalanine, L Ala—Alanine, L Lys—Lysine, L Asp—Aspartic Acid, L Cys—Cysteine, L Arg—Arginine, L Gln—Glutamine, L Pro—Proline, L Leu—Leucine, L Met—Methionine, L Ser—Serine, L Asn—Asparagine, L His—Histidine, L Trp—Tryptophan, L Val—Valine, L Orn—Ornithine, Desamino Tyr—Desamino Tyrosine, Desamino His—Desamino Histidine, Desamino alpha Aib—Desamino alpha aminoisobutyric acid, Desamino alpha Abu—Desamino alpha aminobutyric acid, Desamino alpha, gamma Abu—Desamino alpha, gamma aminobutyric acid.

Moreover, all of the three letter-abbreviations of the amino acids preceded by a "D" indicate the dextro-isomer of the amino acid residue, and glycine is considered to be included in the term naturally occurring L-amino acids. Other abbreviations used herein include: Aib—aminoisobutyric acid, inip—isonipecotyl, Abu—aminobutyric acid, alpha Nal—alpha-naphthylalanine, beta Nal—beta-naphthylalanine, D alpha Nal—alpha-naphthyl-D-alanine, D beta Nal—beta-naphthyl-D-alanine, Pal 3-pyridyl alanine, CHx—cyclohexyl, CHxAla—L-cyclohexylalanine, Ava—Aminovaleric acid, IMA—N alpha-imidazole acetic acid, imc—imidazole carboxylic acid, beta Ala—beta-Alanine, ILys—Lysine (iPr) which is isopropylαN$^ε$lysine, α,γAbu—alpha gamma diaminobutyric acid, Nle—norleucine, PicLys—Nε-picoloyl-lysine, inip—isonipecotoc carboxylic acid, NMePhe—methylated phenylalanine amino nitrogen, Sar—sarcosine (N-methylglycine), <Glu—pyroglutamic acid, AcDβNal—acetylated D beta-naphthylalanine, and AcDαNal—acetylated D alpha-naphthylalanine, NAcDβNal—acetyl N-Dβ-Naphthylalanine.

In one embodiment, the ghrelin receptor antagonist has the formula: A$_7$-A$_8$-A$_9$-A$_{10}$ (Formula II) as described more fully above. Examples of antagonist compound of formula II are shown in Tables 4-8. The preferred antagonist has the formula αγAbu-DTrp-DTrp-(Ser/Lys/Orn)-NH$_2$. A few select examples include: Tyr-DAla-Phe-Aib-NH$_2$; Tyr-DAla-Sar-NMePhe-NH$_2$; Lys-DHis-DTrp-Phe-NH$_2$; γAbu-DTrp-DTrp-Orn-NH$_2$; inip-Trp-Trp-Phe-NH$_2$; Ac-DTrp-Phe-DTrp-Leu-NH$_2$; Ac-DTrp-DTrp-Lys-NH$_2$; Ac-DβNal-Leu-Pro-NH$_2$.

In another embodiment, the antagonist compound has a formula other than the preferred αγAbu-DTrp-DTrp-(Ser/Lys/Orn)-NH$_2$. Pharmaceutically acceptable organic and inorganic addition salts thereof are also included.

A compound having the formula S$^1$B$^1$S$^2$B$^2$S$^3$, wherein S$^1$ is R$^1$, R$^1$R$^2$, R$^1$R$^2$R$^3$, H or COOH, wherein R$^1$, R$^2$ and R$^3$ are selected from the group consisting of any natural L amino acid, Pal (3-pyridyl alanine), cyclo-Ala, Aib, Nle, inip, Abu, βNal, αNal, Orn, carboxylic acid and their respective D isomers;

B$^1$ is selected from the group consisting of Trp, βNal, αNal, Leu, Lys, cyclohexyl Ala and their respective D isomers;

S$^2$ is des Amino, R$^1$, R$^1$R$^2$, R$^1$R$^2$R$^3$, H or COOH, wherein R$^1$, R$^2$ and R$^3$ are as defined above;

B$^2$ is any natural L amino acid, Pal (3-pyridyl alanine), cycloAla, Aib, Nle, inip, Abu, βNal, αNal, Orn and their respective D isomers; and S$^3$ is NH$^2$, COOH, R$^1$, R$^1$R$^2$, R$^1$R$^2$R$^3$, wherein R$^1$, R$^2$ and R$^3$ are as defined above, or pharmaceutically acceptable salts thereof.

In other embodiments, the compound can be a dipeptide, a tripeptide and/or a tetrapeptide. Examples of such peptides include, but are not limited to, the following embodiments.

In one embodiment, the ghrelin receptor antagonist has at least a tetrapeptide core of DTrp-Ala-Trp-DPhe. The position 1 of the tetrapeptide core comprise DTrp, DβNal, DαNal, DPhe, and DcyclohexylAla, while the position 2 of the tetrapeptide core comprise L or D natural or unnatural or derivatized amino acid residues including but not exclusive to DLys, DOrn, Ser, DPal, DLeu, Phe. In one embodiment, there may be additional amino acids at the N-terminus alone, C-terminus alone, or N- and C-termini of the tetrapeptide core. N terminus additions may comprise of L or D natural derivative amino acids such as—Tyr, His, desamino Tyr, GlyψAlaψ, DAla, βAla, α, γ, αγAbu, DLys, <Glu, DArg, DOrn or carboxylic acid or mono, di tripeptides or longer peptides such as His-Lys, His-DLys, DHis-Lys. The C-terminus additions may comprise of L or D natural or unnatural amino acid residues with terminal amidation or carboxylation including mono, di, tripeptides or longer peptides such as Lys, Arg, Lys-Gln, Lys-Gln-Gly. Examples of tetrapeptide core containing antagonist are DHis-DTrp-DPro-DIleNH$_2$, DHis-DTrp-DPro-DArgNH$_2$, and DβNal-DTrp-DPro-DArgNH$_2$.

In one embodiment, the ghrelin receptor antagonist has at least a tripeptide core of DAla-DTrp-Phe. The positions 1 and 2 of this tripeptide core may be substituted with any amino acids selected from D amino acid residues or unnatural amino acid residues. The position 3 position may be substituted with amino acids selected from Trp, Leu, Val, Ile, Pro, Phe, cyclohexylAla and cyclopentylAla. In one embodiment, there may be additional amino acids at the N-terminus alone, C-terminus alone, or at both N- and C-terminus of the tripeptide core. N terminus additions may comprise L or D natural or unnatural amino acid residues and/or organic carboxylic acid, dipeptides or longer peptides with L or D natural or unnatural amino acid residues in various combinations and/or sequences including but not limited to DAla-DβNal, DAla-DαNal, βAla-Trp, His-Trp, DHis-Trp, DHis-DTrp, His-DTrp. C terminus additions may comprise L or D natural or unnatural amino acid residues with terminal amidation or carboxylation including, but are not limited to, mono, di, tripeptides or longer peptides such as Lys, Arg, Lys-Gln, Lys-Gln-Gly or carboxylic acid. Examples of tripeptide core containing antagonist are αAib-DTrp-cyclohexylDAlaNH$_2$, NAcDTrp-DTrpLysNH$_2$ and NAcDβNal-Leu-ProNH$_2$.

In one embodiment, the ghrelin receptor antagonist has at least a tripeptide core of DTrp-Phe-DTrp. The positions 1 and 3 of this core may be substituted with amino acids selected from DβNal, DαNal, DPhe, and DcyclohexylAla, and the position 2 of the tripeptide core may be substituted with amino acids selected from Trp βNal, αNal, Leu, DLeu, and DLys. In one embodiment, there may be additional amino acids at the N-terminus alone, C-terminus alone, or at both N- and C-terminus of the tripeptide core. N terminus additions may comprise a L or D natural or unnatural amino acid residues or organic carboxylic acid. N terminus additions may comprise a dipeptides, tripeptide, or tetrapeptides comprising L or D natural or unnatural amino acid residues in various combinations and/or sequences, for example DAla-DβNal, DAla-DαNal, βAla-Trp, His-Trp, DHis-Trp, DHis-DTrp, His-DTrp. C terminus additions may comprise an amino acid residue selected from Leu, Lys, and Arg. C terminus additions may also comprise a dipeptide or tripeptide comprising the amino acids Leu, Lys, Arg, and combinations thereof. Examples of C terminus additions are Leu, Leu-Leu, Leu-Lys, Leu-Arg, Leu-Leu-Lys.

In yet another embodiment, the ghrelin receptor antagonist has at least a dipeptide core of DTrp-DTrp wherein the core amino acids may be substituted with D natural and/or derivatized amino acid residues of Trp, βNal, αNal, Phe, and various combinations thereof. In one embodiment, there may be additional amino acids at the N-terminus alone, C-terminus alone, or at both the N- and C-terminus of the dipeptide core. N terminus additions may comprise L or D natural or derivatized amino acid residues and/or organic carboxylic acid. Additionally, N terminus additions may also comprise a dipeptide or tripeptide or tetrapeptide or pentapeptide comprising amino acid residues selected from Tyr, His, desamino Tyr, Lys, Glyψ, Alaψ, DAla, αγAbu, αAbu, γAbu, Lys, DLys, isonipecotic carboxylic acid (inip), βAla, DAla, DLys, DThr, DVal, DLeu, cyclohexylAla, cyclopentylAla, DTrp, iPrLys, and diethyl guanidinoArg. Examples of N-terminus additions include His-Trp, DLys-Tyr, βAla-Trp, N-AcDLys-Tyr, βAla-Pal, αγAbu-Trp, γAbu-Trp, Ava-Trp, αAbu-Trp, His-DLys, Lys-DHis, DLys-Tyr-DHis. C terminus additions may comprise L or D natural or derivatized amino acid residues or organic carboxylic acids. C terminus additions may also comprise a dipeptide or tripeptide or tetrapeptide or pentapeptide comprising amino acids residues selected from Phe, DPro, Leu, Met, Ser, Lys, Orn, Arg, cyclohexylAla, and cyclopentylAla. examples of the C-terminus additions are Phe-Lys, DPro-Lys, Phe-DPro-Lys, DPro-Arg, Phe-Met, Phe-Ala, Phe-Ser. Examples of dipeptide core containing antagonist are NAcDβNal-DTrpNH$_2$ and DThr-DαNal-DTrp-DPro-ArgNH$_2$.

In one embodiment, the ghrelin receptor antagonist compound has a formula (Formula III) as described in detailed above:

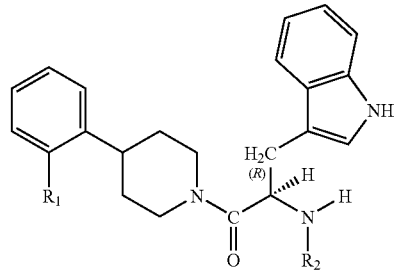

Examples of ghrelin receptor antagonist compounds having the formula III are shown in Tables 10 and 11.

In one embodiment, the ghrelin receptor antagonist compounds having the formula III are:

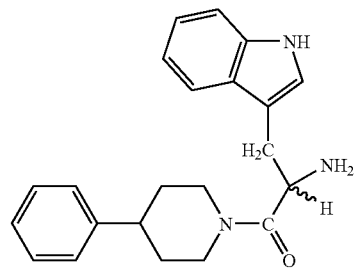 [SMILES: NC(Cc1c[nH]c2ccccc12)C(=O)N1CCC(c2ccccc2)CC1]

(R)-2-amino-3-(1H-indol-3-yl)-1-(4-phenylpiperidin-1-yl)propan-1-one

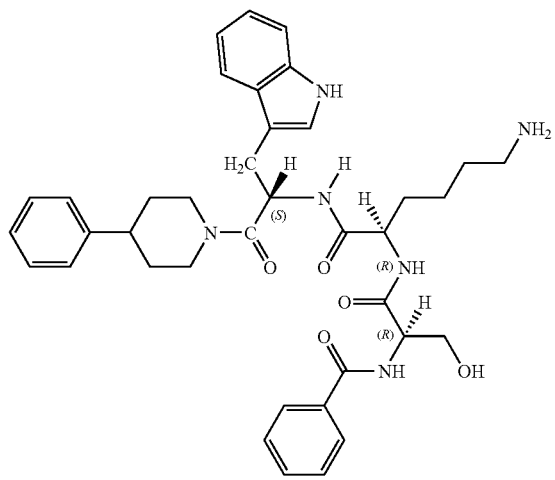

N—((R)-1-((R)-1-((S)-3-(1H-indol-3-yl)-1-oxo-1-(4-phenylpiperidin-1-yl)propan-2-ylamino)-6-amino-1-oxohexan-2-ylamino)-3-hydroxy-1-oxopropan-2-yl)benzamide

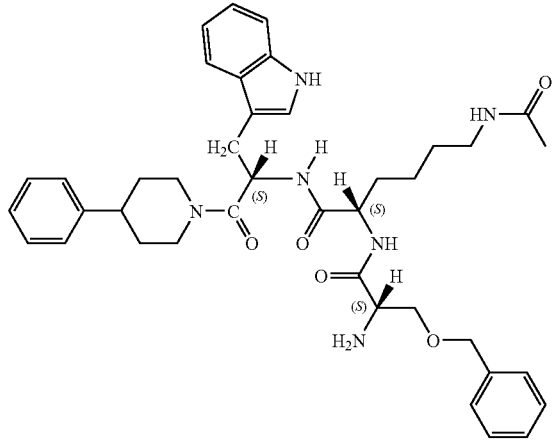

(S)—N—((S)-3-(1H-indol-3-yl)-1-oxo-1-(4-phenylpiperidin-1-yl)propan-2-yl)-6-acetamido-2-((S)-2-amino-3-(benzyloxy)propanamido)hexanamide

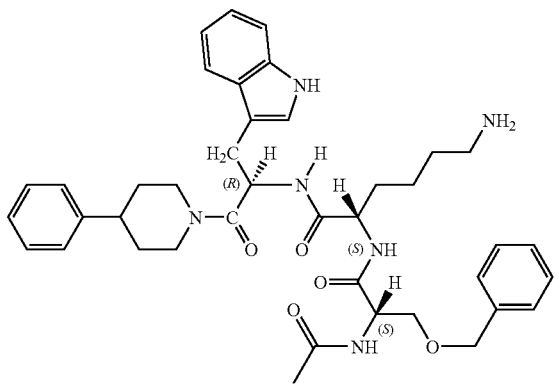

(S)—N—((R)-3-(1H-indol-3-yl)-1-oxo-1-(4-phenylpiperidin-1-yl)propan-2-yl)-2-((S)-2-acetamido-3-(benzyloxy)propanamido)-6-aminohexanamide

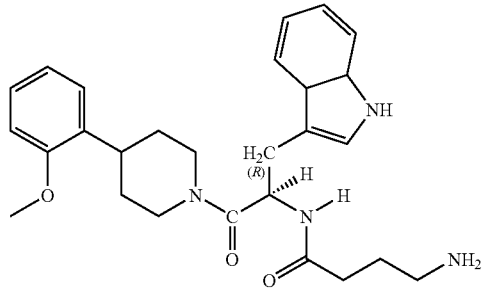 [SMILES: COc1ccccc1C1CCN(C(=O)[C@@H](CC2=CNC3C=CC=CC23)NC(=O)CCCN)CC1]

(R)—N-(3-(1H-indol-3-yl)-1-(4-(2-methoxyphenyl)piperidin-1-yl)-1-oxopropan-2-yl)-4-aminobutanamide

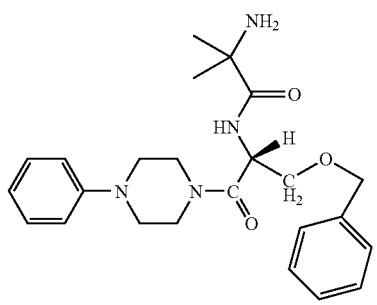 [SMILES: CC(C)(N)C(=O)N[C@H](COCc1ccccc1)C(=O)N1CCN(c2ccccc2)CC1]

(R)-2-amino-N-(3-(benzyloxy)-1-oxo-1-(4-phenylpiperazin-1-yl)propan-2-yl)-2-methylpropanamide In one embodiment, the isomers of ghrelin receptor antagonist compounds of formula III are included.

In another embodiment, the ghrelin receptor antagonist compound has a formula (Formula IV) as described in detailed above:

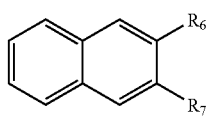

Examples of ghrelin receptor antagonist compounds having the formula IV are shown in Tables 10 and 11.

In one embodiment, the ghrelin receptor antagonist compounds having the formula IV are:

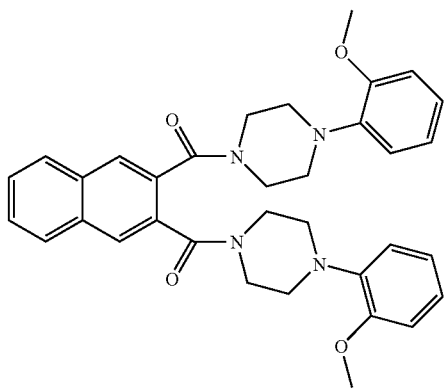 [SMILES: COc1ccccc1N1CCN(C(=O)c2cc3ccccc3cc2C(=O)N2CCN(c3ccccc3OC)CC2)CC1]

naphthalene-2,3-diylbis((4-(2-methoxyphenyl)piperazin-1-yl)methanone)

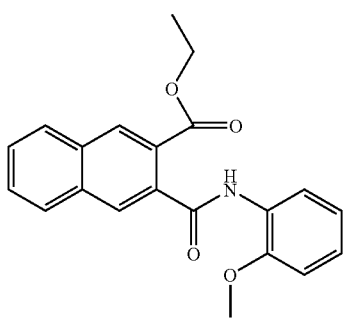 [SMILES: CCOC(=O)c1cc2ccccc2cc1C(=O)Nc1ccccc1OC]

3-(2-methoxyphenylcarbamoyl)-2-naphthoate

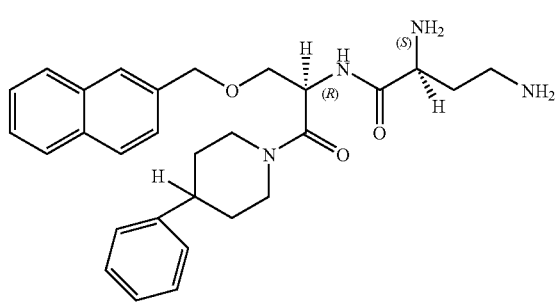

(S)-2,4-diamino-N—((R)-3-(naphthalen-2-ylmethoxy)-1-oxo-1-(4-phenylpiperidin-1-yl)propan-2-yl)butanamide

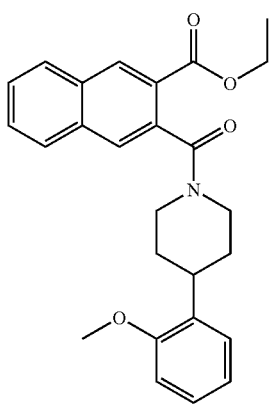 [SMILES: CCOC(=O)c1cc2ccccc2cc1C(=O)N1CCC(c2ccccc2OC)CC1]

ethyl 3-(4-(2-methoxyphenyl)piperidine-1-carbonyl)-2-naphthoate

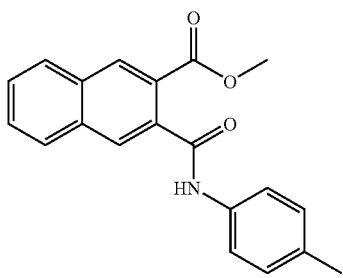 [SMILES: COC(=O)c1cc2ccccc2cc1C(=O)Nc1ccc(C)cc1]

methyl 3-(p-tolylcarbamoyl)-2-naphthoate

In one embodiment, the isomers of ghrelin receptor antagonist compounds of formula IV are included.

In yet another embodiment, the ghrelin receptor antagonist compound has a formula (Formula V) as described in detailed above:

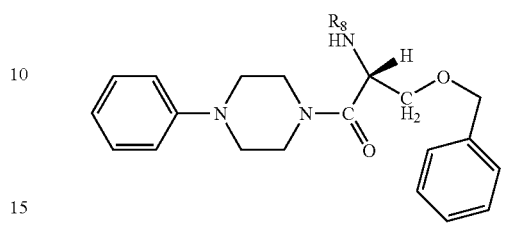

Examples of ghrelin receptor antagonist compounds having the formula V are shown in Tables 10 and 11.

In one embodiment, the ghrelin receptor antagonist compounds having the formula V are:

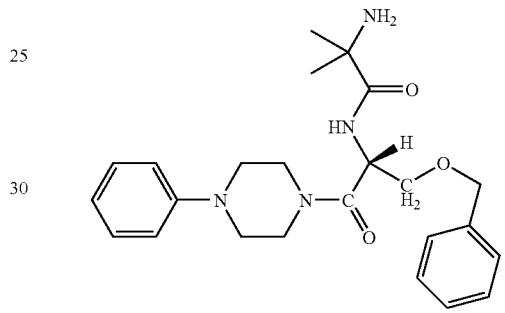

(R)-2-amino-N-(3-(benzyloxy)-1-oxo-1-(4-phenylpiperazin-1-yl)propan-2-yl)-2-methylpropanamide

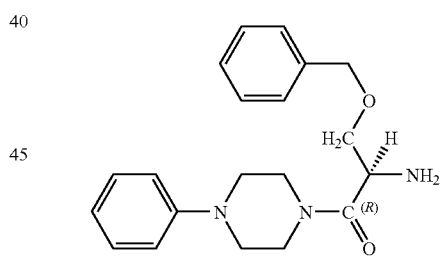

(R)-2-amino-3-(benzyloxy)-1-(4-phenylpiperazin-1-yl)propan-1-one

In one embodiment, the isomers of ghrelin receptor antagonist compounds of formula V are included.

In one embodiment, the compound has a formula:
$AA_1$-$AA_2$-$AA_3$-$AA_4$-$AA_5$-$AA_6$ (Formula I'), wherein $A_1$ is His, Gly, αAib (alpha-aminoisobutyric acid), γAbu (gamma-aminobutyric acid), or α,γAbu (alpha, gamma-diaminobutyric acid or 2,4-diaminobutyric acid). There can be a normal or reduced psi (ψCH$_2$NH) peptide bond between positions 1 and 2. Alternatively, $AA_1$ may be amino acids with methylation of the terminal nitrogen of the alpha carbon atom of the $A_1$ residue when a terminal nitrogen is present at the α carbon atom;

$AA_2$ is Dα,βnaphthylalanine, DTrp, DPhe, or DCyclohexylalanine, wherein $AA_2$ is with or without methylation of the terminal nitrogen of the α carbon atom of the $AA_2$ residue.

In one embodiment, AA$_2$ could have extended aromatic chains, such as, for example, D-4-halo-Phe, D-4-pyrolidylalanine, homologues and analogues thereof, wherein AA$_2$ is with or without methylation of the terminal nitrogen of the α carbon atom of the AA$_2$ residue;

AA$_3$ is D or L Lys, Arg, Orn, or α,γAbu;

AA$_4$ is D or L Trp, Phe, or Cyclohexylalanine;

AA$_5$ is DPhe or DCyclohexylalanine; and

AA$_6$ is Lys, Arg, Orn, or α,γAbu, or pharmaceutically acceptable salts thereof, wherein the AA$_6$ residue can be present either in a C terminal amidated form or as a free carboxylic acid.

Unless otherwise defined herein, scientific and technical terms used in connection with the present application shall have the meanings that are commonly understood by those of ordinary skill in the art.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

The novel antagonists embodied in the invention can be synthesized according to the usual methods of solution and solid phase peptide chemistry, or by classical methods known in the art. Purification of peptides is well known in the art and can be, for example, HPLC. Methods describing useful peptide synthesis and purification methods can be found, for example, in U.S. Patent Application No. 20060084607.

In another embodiment of the present invention, methods for the treatment of various diseases and disorders such as obesity, overeating, diabetes, unregulated cellular proliferation, and cancer using the novel compounds of the present invention are encompassed. In such embodiments, the novel ghrelin receptor antagonists of the present invention are administered to an individual in need of such treatment.

In one embodiment, the invention provides use of the ghrelin receptor antagonist compounds as described throughout the specification for the treatment of obesity, overeating, diabetes mellitus, metabolic syndrome, unregulated cellular proliferation, and cancer. In one preferred embodiment, the invention provides use of the ghrelin compound for the treatment of obesity alone or in combination with other obesity treatments.

In one preferred embodiment, use of the ghrelin receptor antagonist compounds, including compositions of compounds having formulae I-V for the treatment of obesity is combined with a surgical or mechanical procedure used to treat obesity. Such procedures include but are not limited to gastric bypass surgery and gastric banding.

In one preferred embodiment, use of the ghrelin receptor antagonist compounds, comprising compositions of compounds having formulae I, II, III, IV or V, or combinations thereof for the treatment of obesity is combined with a surgical or mechanical procedure used to treat obesity. Such procedures include but are not limited to gastric bypass surgery and gastric banding.

In one preferred embodiment, use of the ghrelin receptor antagonist compounds, consisting essentially of compositions of compounds having formulae I, II, III, IV or V, or combinations thereof for the treatment of obesity is combined with a surgical or mechanical procedure used to treat obesity. Such procedures include but are not limited to gastric bypass surgery and gastric banding.

In one preferred embodiment, use of the ghrelin receptor antagonist compounds, consisting of compositions of compounds having formulae I, II, III, IV or V, or combinations thereof for the treatment of obesity is combined with a surgical or mechanical procedure used to treat obesity. Such procedures include but are not limited to gastric bypass surgery and gastric banding.

In another embodiment, the invention provides for the use of the ghrelin compounds, including compositions of compounds having formulae I, II, III, IV or V, or combinations thereof, for the treatment, prevention, or management of hormonally functional endocrine or non-endocrine tumors.

In one embodiment, compositions of compounds having formulae I, II, III, IV or V, or combinations thereof can be used in combination for the treatment of various diseases and disorders.

The experimental data regarding the effect of the compounds of this invention has been produced in well known animal models that are typically used for the effects of anti-obesity treatments at the first stage and are thus likely to be applicable to human obesity.

The invention provides novel compounds including:

A compound with the formula Tyr-DTrp-DLys-Trp-DPhe-NH$_2$, Tyr-DTrp-Lys-Trp-DPhe-NH$_2$, His-DTrp-DLys-Trp-DPhe-NH$_2$, His-DTrp-DLys-Phe-DTrp-NH$_2$, His-DTrp-DArg-Trp-DPhe-NH$_2$, His-DTrp-DLys-Trp-DPhe-Lys-NH$_2$, DesaminoTyr-DTrp-Ala-Trp-DPhe-NH$_2$, DesaminoTyr-DTrp-DLys-Trp-DPhe-NH$_2$, DesaminoTyr-DTrp-Ser-Trp-DPhe-Lys-NH$_2$, DesaminoTyr-DTrp-Ser-Trp-DPhe-NH$_2$, His-DTrp-DTrp-Phe-Met-NH$_2$, Tyr-DTrp-DTrp-Phe-Phe-NH$_2$, Glyψ[CH$_2$NH]-DβNal-Ala-Trp-DPhe-Lys-NH$_2$, Glyψ[CH$_2$NH]-DβNal-DLys-Trp-DPhe-Lys-NH$_2$, DAla-DβNal-DLys-DTrp-Phe-Lys-NH$_2$, His-DβNal-DLys-Trp-DPhe-Lys-NH$_2$, Ala-His-DTrp-DLys-Trp-DPhe-Lys-NH$_2$, Alaψ[CH$_2$NH]-DβNal-Ala-Trp-DPhe-Lys-NH$_2$, DβNal-Ala-Trp-DPhe-Ala-NH$_2$, DAla-DcyclohexylAla-Ala-Phe-DPhe-Nle-NH$_2$, DcyclohexylAla-Ala-Phe-DTrp-Lys-NH$_2$, DAla-DβNal-Ala-Thr-DThr-Lys-NH$_2$, DcyclohexylAla-Ala-Trp-DPhe-NH$_2$, DAla-DβNal-Ala-Ala-DAla-Lys-NH$_2$, DβNal-Ala-Trp-DPhe-Leu-NH$_2$, His-DTrp-Phe-Trp-DPhe-Lys-NH$_2$, DAla-DβNal-DAla-DTrp-Phe-Lys-NH$_2$, βAla-Trp-DAla-DTrp-Phe-NH$_2$, His-Trp-DAla-DTrp-Phe-LysNH$_2$, DLys-DβNal-Ala-Trp-DPhe-Lys-NH$_2$, DAla-DβNal-DLys-DTrp-Phe-Lys-NH$_2$, Tyr-DAla-Phe-Aib-NH$_2$, Tyr-DAla-Sar-NMePhe-NH$_2$, α,γAbu-DTrp-DTrp-Ser-NH$_2$, α,γAbu-DTrp-DTrp-Lys-NH$_2$, α,γAbu-DTrp-DTrp-Orn-NH$_2$, αAbu-DTrp-DTrp-Orn-NH$_2$, DThr-DαNal-DTrp-DPro-Arg-NH$_2$, DAla-Ala-DAla-DTrp-Phe-Lys-NH$_2$, Alaψ[CH$_2$NH]His-DTrp-Ala-Trp-DPhe-Lys-NH$_2$, Lys-DHis-DTrp-Phe-NH$_2$, γAbu-DTrp-DTrp-Orn-NH$_2$, inip-Trp-Trp-Phe-NH$_2$, AcDTrp-Phe-DTrp-Leu-NH$_2$, AcDTrp-Phe-DTrp-Lys-NH$_2$, AcDTrp-DTrp-Lys-NH$_2$, DLys-Tyr-DTrp-DTrp-Phe-Lys-NH$_2$, AcDβNal-Leu-Pro-NH$_2$, βAla-Trp-DTrp-DTrp-Orn-NH$_2$, DVal-DαNal-DTrp-Phe-Arg-NH$_2$, DLeu-DαNal-DTrp-Phe-Arg-NH$_2$, CyclohexylAla-DαNal-DTrp-Phe-Arg-NH$_2$, DTrp-DαNal-DTrp-Phe-Arg-NH$_2$, DAla-DβNal-DPro-Phe-Arg-NH$_2$, AcDαNal-DTrp-Phe-Arg-NH$_2$, DαNal-DTrp-Phe-Arg-NH$_2$, His-DTrp-DTrp-Lys-NH$_2$, AcDβNal-DTrp-NH$_2$, αAib-DTrp-DcyclohexylAla-NH$_2$, αAib-DTrp-DAla-cyclohexylAla-NH$_2$, DAla-DcyclohexylAla-Ala-Ala-Phe-DPhe-Nle-NH$_2$, DPhe-Ala-Phe-DPal-NH$_2$, DPhe-Ala-Phe-DPhe-Lys-NH$_2$, DLys-Tyr-DTrp-DTrp-Phe-NH$_2$, AcDLys-Tyr-DTrp-DTrp-Phe-NH$_2$, Arg-DTrp-Leu-Tyr-Trp-Pro, AcDβNal-PicLys-ILys-DPhe-NH$_2$, DPal-Phe-DTrp-Phe-Met-NH$_2$, DPhe-Trp-DPhe-Phe-Met-NH$_2$, DPal-Trp-DPhe-Phe-Met-NH$_2$, βAla-Pal-DTrp-DTrp-Orn-NH$_2$, α,γAbu-Trp-DTrp-DTrp-Orn-NH$_2$, βAla-Trp-DTrp-DTrp-Lys-NH$_2$, γAbu-Trp-DTrp-DTrp-Orn-NH$_2$, Ava-Trp-DTrp-DTrp-Orn-NH$_2$, DLys-Tyr-DTrp-Ala-Trp-DPhe-NH$_2$, His-DTrp-DArg-Trp-DPhe-NH$_2$, <Glu-His-Trp- DSer-DArg-NH$_2$, DPhe-DPhe-DTrp-Met-DLys-NH$_2$, O-(2-methylallyl)benzophenone oxime, (R)-2-amino-3-(1H-indol-3-yl)-1-(4-phenylpiperidin-1-yl)propan-1-one, N—((R)-1-((R)-1-((S)-3-(1H-indol-3-yl)-1-oxo-1-(4-phenylpiperidin-1-yl)propan-2-ylamino)-6-amino-1-oxohexan-2-ylamino)-3-hydroxy-1-oxopropan-2-yl)benzamide, (S)—N—((S)-3-(1H-indol-3-yl)-1-oxo-1-(4-phenylpiperidin-1-yl)propan-2-yl)-6-acetamido-2-((S)-2-amino-3-(benzyloxy)propanamido)hexanamide, (S)—N—((R)-3-(1H-indol-3-yl)-1-oxo-1-(4-phenylpiperidin-1-yl)propan-2-yl)-2-((S)-2-acetamido-3-(benzyloxy)propanamido)-6-aminohexanamide, (R)—N-(3-(1H-indol-3-yl)-1-(4-(2-methoxyphenyl)piperidin-1-yl)-1-oxopropan-2-yl)-4-aminobutanamide, (R)—N-(3-(1H-indol-3-yl)-1-(4-(2-methoxyphenyl)piperidin-1-yl)-1-oxopropan-2-yl)-2-amino-2-methylpropanamide, methyl 3-(p-tolylcarbamoyl)-2-naphthoate, ethyl 3-(4-(2-methoxyphenyl)piperidine-1-carbonyl)-2-naphthoate, 3-(2-methoxyphenylcarbamoyl)-2-naphthoate, (S)-2,4-diamino-N—((R)-3-(naphthalen-2-ylmethoxy)-1-oxo-1-(4-phenylpiperidin-1-yl)propan-2-yl)butanamide, naphthalene-2,3-diylbis((4-(2-methoxyphenyl)piperazin-1-yl)methanone), (R)-2-amino-N-(3-(benzyloxy)-1-oxo-1-(4-phenylpiperazin-1-yl)propan-2-yl)-2-methylpropanamide, (R)-2-amino-3-(benzyloxy)-1-(4-phenylpiperazin-1-yl)propan-1-one or pharmaceutically acceptable salts, prodrugs, or active metabolites thereof.

Uses of these compounds for the modulation, specifically inhibition of ghrelin receptor are also provided.

Additionally, the invention provides uses of these compounds for the treatment of diseases wherein inhibition of ghrelin receptor is advantageous. Such diseases include but are not limited to obesity, diabetes mellitus, metabolic syndrome or certain types of cancer as described in this specification.

Thus, in connection with the administration of a novel compound of the invention, e.g. a ghrelin receptor antagonist, a compound which is "effective against" a disease or disorder indicates that administration in a clinically appropriate manner results in a beneficial effect for at least a statistically significant fraction of patients, such as a improvement of symptoms, a cure, a reduction in symptoms or disease load, reduction in tumor mass or cell numbers, extension of life, improvement in quality of life, or other effect generally recognized as positive by medical doctors familiar with treating the particular type of disease or condition.

The therapeutic compositions of this invention may be administered intravenously (i.v.), as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle. Suitable therapeutic vehicle include, but not limited to, sterile saline, buffered phosphate saline, lactated Ringer's saline.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

The compositions of the invention comprising the ghrelin receptor antagonists having the formulae I-V can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

The amount of ghrelin receptor antagonist or combination of compounds of the present invention administered will vary depending on numerous factors, e.g., the particular animal treated, its age and sex, the desired therapeutic affect, the route of administration and which polypeptide or combination of polypeptides are employed. In all instances, however, a dose effective (therapeutically effective amount) to promote inhibition of growth hormone level in the blood of the recipient animal is used. The dose will depend on a combination of factors, i.e., antagonist receptor action(s), potency, efficacy, pharmacokinetics, pharmacodynamics, route of administration, method of administration and clinical disorder and/or metabolic status. Generally, dosage levels of between 0.0001 to 100 mg/kg of body weight daily are administered to patients and mammals in need to obtain effective inhibition of growth hormone in the blood. The preferred amount can readily be determined empirically by the skilled artisan.

When combinations of ghrelin receptor antagonist compounds are used, lower amounts of the antagonist may be used in the treatment of diseases and disorders. This occurs when one compound exhibit synergistic effect over the activity of a second compound when used in combination.

In another embodiment, the compounds of the inventions may be used in combination with other treatment regime for treating the diseases and disorders associated with obesity, overeating, diabetes, unregulated cellular proliferation, and cancer.

The compounds of the present invention may be formulation for sustained or controlled release. The antagonists of the present invention may be admixed with biologically compatible polymers or matrices which control the release rate of the antagonists into the immediate environment. Controlled or sustained release compositions include formulation in lipophilic depots (e.g., fatty acids, waxes, oils). Also contemplated by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral.

Controlled release permits dosages to be administered over time, with controlled release kinetics. In some instances, delivery of the therapeutic agent is continuous to the site where treatment is needed, for example, over several weeks. Controlled release over time, for example, over several days or weeks, or longer, permits continuous delivery of the therapeutic agent to obtain optimal treatment. The controlled delivery vehicle is advantageous because it protects the therapeutic agent from degradation in vivo in body fluids and tissue, for example, by proteases.

Controlled release from the pharmaceutical formulation may be designed to occur over time, for example, for greater than about 12 or 24 hours. The time of release may be selected, for example, to occur over a time period of about 12 hours to 24 hours; about 12 hours to 42 hours; or, e.g., about 12 to 72 hours. In another embodiment, release may occur for example on the order of about 2 to 90 days, for example, about 3 to 60 days. In one embodiment, the therapeutic agent is delivered locally over a time period of about 7-21 days, or about 3 to 10 days. In other instances, the therapeutic agent is administered over 1, 2, 3 or more weeks in a controlled dosage. The controlled release time may be selected based on the condition treated.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

Compositions comprising an effective amount of a ghrelin receptor antagonist of the present invention, in combination with other components, such as a physiologically acceptable diluent, carrier, or excipient, are provided herein. The antagonists can be formulated according to known methods used to prepare pharmaceutically useful compositions. They can be combined in admixture, either as the sole active material or with other known materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in Remington's Pharmaceutical Sciences, $16^{th}$ ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

Treatment of Diseases and Disorders

In one embodiment, a method to treat obesity is encompassed. In particular, the present invention comprises methods for regulating food intake in a human subject; for improving a compliance of a human subject to caloric restriction; and for reducing a desire of a human subject to consume an over-abundance of calories and/or fats. This method comprises the administration of novel ghrelin receptor antagonists as described above.

The present invention further provides a method for preventing or reducing weight gain in a human subject, by administration of ghrelin receptor antagonists that have a pharmacological half-life that allows an efficient treatment regime thereof.

Also encompassed are methods for reducing a desire of a human subject to consume calories following gastric banding or gastric bypass surgery, by administration of ghrelin receptor antagonists of the present invention.

In addition to the obesity related disorders discussed above, the ghrelin receptor antagonist compositions of the present invention are useful in the treatment or prevention of the following obesity related diseases and/or disorders: overeating; bulimia; hypertension; diabetes, elevated plasma insulin concentrations; insulin resistance; dyslipidemias; hyperlipidemia; endometrial, breast, prostate and colon cancer; osteoarthritis; obstructive sleep apnea; cholelithiasis; gallstones; abnormal heart rhythms; heart arrythmias; myocardial infarction; congestive heart failure; coronary heart disease; sudden death; stroke; polycystic ovarian disease; craniopharyngioma; the Prader-Willi Syndrome; Frohlich's syndrome; GH-deficient subjects; normal variant short stature; Turner's syndrome; and other pathological conditions showing reduced metabolic activity or a decrease in resting energy expenditure as a percentage of total fat-free mass, e.g., children with acute lymphoblastic leukemia.

The present invention also encompasses the treatment of obesity and obesity related diseases and disorders by administering a combination of a ghrelin receptor antagonist and an anti-obesity agent, which may be administered separately or concurrently.

Anti-obesity agents to be used in combination with the ghrelin receptor antagonists of the present invention are known to those of skill in the art and may include, but are not limited to, a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, leptin, a leptin derivative, an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, a GHS (growth hormone secretagogue receptor) agonist, a 5HT2C (serotonin receptor 2C) agonist, a Mc4r (melanocortin 4 receptor) agonist, a monoamine reuptake inhibitor, an UCP-1 (uncoupling protein-1), 2, or 3 activator, a β3 (beta adrenergic receptor 3) agonist, a thyroid hormone β agonist, a PDE (phosphodiesterase) inhibitor, a FAS (fatty acid synthase) inhibitor, a DGAT1 (diacylglycerol acyltransferase) inhibitor, a DGAT2 inhibitor, an ACC2 (acetyl-CoA carboxylase-2) inhibitor, a glucocorticoid antagonist, an acyl-estrogen, a lipase inhibitor, a fatty acid transporter inhibitor, a dicarboxylate transporter inhibitor, a glucose transporter inhibitor, a serotonin reuptake inhibitors, metformin, and topiramate.

The anti-obesity compound to be used in combination with the novel ghrelin receptor antagonists of the present invention may act via a mechanism other than ghrelin, thus providing for additive anti-obesity effects.

In one embodiment, the novel ghrelin receptor antagonist of the present invention is administered prior to taking a meal, for example, 4 hours, 3 hours, 2 hours, 1 hour, or 0.5 hours prior to expected meal time. Preferably, the ghrelin receptor antagonist is administered 0.5 hours prior to feeding. Alternatively, the ghrelin receptor antagonist may be administered continuously, for example, systemically, as a single administration every 6, 5, 4, 3, 2, or 1 month, preferably every 3 months. Here, the novel ghrelin receptor antagonist of the present invention may normalize an otherwise dysfunctional endocrine system. The compound may be active in the individual for several months.

In another embodiment of the present invention, a method for treating diabetes is encompassed. Diabetes may include both insulin-dependent diabetes mellitus (i.e., IDDM, also known as type I diabetes) and non-insulin-dependent diabetes mellitus (i.e., NIDDM, also known as Type II diabetes). In this method, individuals with or at risk for developing diabetes are administered the ghrelin receptor antagonists of the present invention alone or in combination with other diabetes treatments known to those of skill in the art.

"Treatment" (of obesity and obesity-related disorders) refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. Another outcome of treatment may be to maintain weight loss. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

In one embodiment, the ghrelin receptor antagonists of the present invention are used to treat or prevent hormonally functional endocrine or non-endocrine tumors.

In one embodiment, the invention provides a method to decrease/regulate gastrointestinal motility/acidity in a mammal, said method comprising use of a compound of claims 1-7.

In another embodiment, the invention provide a method of treatment, prevention or management of psychobehavior related to under and over nutrition such as hunger, satiety and anxiety.

In yet another embodiment, the invention provides a method for augmenting the actions of desacyl ghrelin by decreasing the action of acyl ghrelin and its receptor, said method comprising use of a compound of claims 1-7.

In another embodiment, the novel ghrelin receptor antagonists are administered to an individual for the treatment of pituitary tumor, e.g. to inhibit pituitary tumor producing growth hormone.

In another embodiment, the novel ghrelin receptor antagonists are administered in conjunction with methods for the treatment of tumors that produce prolactin. Prolactin ("PRL") is a 23-kDa neuroendocrine hormone which is structurally related to growth hormone. Prolactin secretion has been associated with several types of cancer including, but not limited to breast and prostrate. Thus, the present invention relates to methods and compositions for inhibiting the cell proliferation-promoting effects of prolactin on its receptor. Conditions which may benefit from the administration of a novel ghrelin receptor antagonist of the invention include both benign and malignant proliferation of cells which express a prolactin receptor. Such conditions include but are not limited to proliferative diseases of the breast, including benign conditions such as breast adenomas and fibrocystic disease, and malignant conditions such as breast cancer, including ductal, scirrhous, medullary, colloid and lobular carcinomas (local or metastatic); and proliferative diseases of the prostate, including benign prostatic hypertrophy and prostate cancer (local or metastatic).

Also encompassed are methods for the treatment of metabolic syndrome. The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III. Metabolic syndrome is obesity related and thus administration of the novel ghrelin receptor antagonists of the present invention are useful in its treatment.

Furthermore, methods for the diagnosis of obesity and obesity related diseases and disorders, including diabetes are encompassed. In this embodiment, the ghrelin receptor antagonist(s) of the present invention are administered to an individual and their response is closely analyzed. A decrease in desire for food immediately following administration of the compounds or a decrease in weight gain or a reduction in weight indicates a propensity to or a current affliction with obesity or an obesity related disease or disorder.

In one embodiment, Ghrelin/GHRP/GHS receptor antagonists can be utilized as a diagnostic agent to assess the role of ghrelin, other ghrelin-like molecules, and ghrelin receptor agonists or its receptor in the regulation of GH secretion, food intake, and gastrointestinal motility. The antagonists can also be used to rule out endogenous pathophysiological activities of ghrelin, assess the role of ghrelin in various physiological and metabolic processes, assess the effects of exogenous ghrelin, GHSs as well as other agents that possibly act via release of endogenous ghrelin or via ghrelin mimics, and determine biological actions of acylated ghrelin over that of desacylated ghrelin.

Specifically, in one embodiment diagnostic indicates/reveals a role of ghrelin and/or its receptor(s) in over, under or dysfunctional secretion in the pathophysiology of GH release. In another embodiment, diagnostic indicates/reveals a role of ghrelin and/or its receptor(s) in the pathophysiology of food intake in over or under nutrition. In yet another embodiment, diagnostic indicates/reveals risk of developing obesity, metabolic syndrome, diabetes and/or success rate of anti-obesity therapy. In yet another embodiment, diagnostic indicates/reveals a role of ghrelin and/or its receptor(s) in cognitive-memory and psychobehavior related to under and/or or nutrition such as hunger, satiety and anxiety. In another embodiment, the diagnostic indicates/reveals role of ghrelin and/or its receptor(s) in the pathophysiology of insulin secretion and/or its actions. In another embodiment, the diagnostic indicates/reveals role of ghrelin and its receptor(s) on the pathophysiology of gastrointestinal (GI) motility, acidity or other GI disorders. In yet another embodiment, the diagnostic method indicates/reveals role of ghrelin and its receptor(s) on endothelial dysfunction in particular related to vasoconstriction and/or insulin actions in particular hypertension, diabetes and metabolic syndrome. In another embodiment, the diagnostic method indicates/reveals role and action of ghrelin and its receptor(s) on hepatic gluconeogenesis and body fat as indicated by effects on circulating glucose, insulin, adipokines, leptin, resistin, adiponectin and plasminogen activator inhibitor. In still another embodiment, the diagnostic indicates/reveals/distinguishes the actions of acylated ghrelin and desacylated ghrelin on selective actions of certain GH secretagogues. In another method, the diagnostic method indicates/reveals a role of ghrelin and its receptor(s) on agents that increase (i.e., anti-depressants, glucocorticoids and other drugs that influence food intake). In still another embodiment, the diagnostic method indicates/reveals a role of ghrelin and its receptor(s) in hormonally functional endocrine and non-endocrine tumors.

Definitions

The terms "administration of" and or "administering" a compound should be understood to mean providing a ghrelin receptor antagonist compound of the invention, a prodrug or an active metabolite of a compound of the invention to a subject in need of treatment.

The term "ghrelin receptor" as used herein includes growth hormone secretagogue receptor, GHS-R1a and subtypes, isoforms and variants thereof.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The term "drug" or "compound" as used herein refers to a chemical entity or biological product, or combination of chemical entities or biological products, administered to a person to treat or prevent or control a disease or condition.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects. The ghrelin receptor antagonists described herein are effective in treating obesity and obesity related diseases and disorders including diabetes and various types of cancer.

A "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. In some circumstances, cancer cells will be in the form of a tumor; such cells may exist locally within an animal, or circulate in the blood stream as independent cells, for example, leukemic cells. Examples of cancer include but are not limited to breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

The term "inverse agonist" as used herein refers to an agent which binds to the same ghrelin receptor binding-site as an agonist for that receptor but exerts the opposite pharmacological effect.

The term "antagonist" is used in the broadest sense, and includes any molecule that partially or fully blocks, inhibits, or neutralizes a biological activity of ghrelin.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

The invention is further illustrated by the following examples which should not be construed as limiting. The contents of all references cited throughout this application, including the U.S. provisional application Ser. No. 60/795, 960 filed Apr. 28, 2006 as well as the figures and tables are incorporated herein by reference.

EXAMPLES

Animals and Experimental Procedures

Adult male Sprague Dawley rats (225-260 g) were purchased from Charles River Canada (St. Constant, Canada) and individually housed on a 12-h light, 12-h dark cycle (lights on, 0600-1800 h) in a temperature (22±1° C.)—and humidity-controlled room. Purina rat chow (Ralston Purina Co., St. Louis, Mo.) and tap water were available ad libitum.

Chronic intracerebroventricular (i.c.v.) and intracardiac venous cannulas were implanted under sodium pentobarbital (50 mg/kg, i.p.) anesthesia using previously described techniques in (2) and (11). The placement of the icv cannulae was verified by both a positive drinking response to i.c.v. carbachol (100 ng/10 µl) injection on the day after surgery and methylene blue dye at the time of death. After surgery, the rats were placed directly in isolation test chambers with food and $H_2O$ freely available until body weight returned to preoperative levels (usually within 5-7 d). During this time the rats were handled daily to minimize any stress associated with handling on the day of the experiment. On the test day, food was removed 1.5 h before the start of sampling and was returned at the end.

The efficacy of GHS-A to antagonize ghrelin's stimulatory action on GH at both central and peripheral sites was examined. For the central experiments, free-moving rats were i.c.v.

injected with either normal saline or GHS-A (5 µg) at 1045 h and, 15 min later (at 1100 h), were subsequently administered ghrelin i.c.v. (500 ng). Both the human ghrelin peptide (provided by Dr. K. Chang, Phoenix Pharmaceuticals, Inc., Belmont, Calif.) and the GHS-A were diluted in normal saline just before use. Blood samples (0.35 ml) were withdrawn every 15 min over a 6-h sampling period (1000-1600 h) from all animals. To document the rapidity of the GH response to ghrelin, an additional blood sample was obtained 5 min after injection of ghrelin. All blood samples were immediately centrifuged, and plasma was separated and stored at −20° C. for subsequent assay of GH. To avoid hemodynamic disturbance, the red blood cells were resuspended in normal saline and returned to the animal after removal of the next blood sample.

For the peripheral experiments, free-moving rats were iv injected with either normal saline or GHS-A (250 µg) at 1045 h and subsequently with ghrelin i.v. (5 µg) at 1100 h. Blood samples were withdrawn from 1000-1600 h, as described above.

For the study designed to assess the involvement of endogenous ghrelin in the genesis of pulsatile GH secretion, free-moving animals were i.c.v.-injected with either normal saline or GHS-A (5 µg) at two different times in the 6-h sampling period: 1045 h and 1345 h. These time points were chosen because they correspond closely to the time of onset of the spontaneous GH secretory episodes, as previously documented in our laboratory (2, 4). Blood samples were withdrawn from 1000-1600 h, as described above; however, no blood sample was withdrawn 5 min after the injections.

The effects of the GHS-A on both spontaneous and ghrelin-induced food intake and body weight gain were investigated. For the spontaneous experiments, the rats were fasted overnight (1600-1100 h next morning) and were i.c.v.-injected with either normal saline or GHS-A (5 µg) at 1100 h. Food intake was monitored on an hourly basis for 5 h after the initial injection (until 1600 h) and subsequently overnight (1600-0900 h next morning). A measured amount of rat chow pellets was placed in the cage every hour. Spillage was collected by placement of a diaper under the rat cages, and total food consumed for each period was calculated by subtracting uneaten food plus spillage from total given. Body weights were recorded daily at 0900 h. The latency to the onset of the first meal after the injection and the duration of that meal were also monitored.

To examine the effect of GHS-A on ghrelin-stimulated food intake, animals were icv injected with either normal saline or GHS-A (5 µg) at 1045 h and subsequently with ghrelin (500 ng) at 1100 h. Food intake was monitored on an hourly basis as described above. In this experiment, food was removed 1.5 h before the start of the test.

All animal-based procedures were approved by the McGill University Animal Care Committee.

Receptor Binding and Calcium Mobilization Studies

The human ghrelin receptor type 1a (GHS-R1a) was expressed in HEK-293 cells, whose cell membranes were subsequently harvested and used in the binding assay. The receptor concentration (Bmax) used in the assay was 2.3 pmol/mg of protein, resulting in a Kd for ghrelin binding of 0.016 nM. The ability of the antagonist to displace 0.009 nM radiolabelled ghrelin was then tested, at a concentration range of 0.1 nM to 10 µM. The binding affinities (Ki) for ghrelin, GHRP-6 and hexarelin in this system were 0.016 nM, 0.58 nM and 0.59 nM respectively.

The ability of the antagonist to mobilize calcium or to inhibit ghrelin-stimulated calcium mobilization was examined using Euroscreen's AequoScreen platform. This method is based on the co-expression in recombinant cell lines of the GHS-R1a and aequorin, a photoprotein capable of detecting calcium concentrations in the lower micromolar range. The agonistic properties of GHS-A were tested at a concentration range of 1 nM to 3 µM, and its capacity to inhibit the calcium mobilized by 22.15 nM ghrelin was tested at a concentration range of 1 nM to 1.5 µM. In this system, ghrelin was found to have an EC50 of 9.33 nM, EC80 of 22.15 nM, and induced maximal activation at a concentration of 100 nM.

The peptides were synthesized by the solid phase method and purified by HPLC. GH was determined by Radioimmunoassay (RIA).

The In Vitro Cell Culture Method

In vitro GH Release-Female rats of the CD-1 strain were housed in a constant temperature room at 24° C. with 14 h light and 10 h darkness. The rats were fed Purina Rat chow and water at libitum. All studies were started between 0800-1000 hours. Pituitaries of mature female Sprague Dawley rats were rapidly removed after decapitation, neurointermediate lobe discarded and then placed in a pH 7.4 buffer. The pituitaries were cut into ~3-mm pieces and then transferred to a flask containing HEPS buffer with trypsin and incubated at 37° C. Cells were triturated several times during this period. After dispersion, the cells were collected by centrifugation, wash with DMEM and placed into culture well. Cell cultures were maintained for 4 days at 37° with 8% $CO_2$ added to the incubator atmosphere. After 4 days in culture, cells were washed with lactated Ringer's solution adjusted to pH 7.2-7.4 and then vehicle, peptide alone or peptide plus stimulator was added to media. Incubation time was 60-120 minutes after which media was removed from each well for GH determination. The GH RIA reagents were distributed by the NIH. Control data was collected from cell cultures treated with only the corresponding vehicle in the absence of peptide or stimulator. Control stimulated data was collected from cell cultures treated with stimulator alone in the absence of any peptide.

The In Vitro Pituitary Incubation Method

Hormonal activities were obtained from in vitro studies using pituitaries of 20 day old CD-1 strain Sprague Dawley female rats. Two pituitaries were incubated for a total of 4-6 hours. Medium was removed each hour for RIA of GH level and fresh medium was added again. After two one hour pre-incubation periods (P1-P2), the vehicle/peptides were added to two one hour incubations (I3-I4). Peptide activity was calculated as the change in the hormonal level (delta) between I3+I4 and P2. For antagonist activity, the incubation was continued for 2 additional hours (I5-I6) where both the peptide and a stimulator of GH secretion was added and the antagonist activity was calculated as the change in the hormonal level (delta) between I5+I6 and P2. The peptides were assayed in triplicate and the hormone was assayed in duplicate. Each value recorded represents the mean of 6. The GH RIA reagents were distributed by the NIH. Control data was collected from isolated pituitary glands treated with only the corresponding vehicle in the absence of peptide or stimulator. Control stimulated data was collected from isolated pituitary glands treated with stimulator alone in the absence of any peptide.

The In Vivo Assay

For the in vivo assay of GH Release in rat, immature female Sprague Dawley rats were obtained from Charles River from Wilmington, Mass. After arrival they were housed at 25° C. with a 14:10 h light:dark cycle. Water and Purina rat chow were available at libitum. Pups were weaned at 21 days of age.

Immature twenty six day old female Sprague Dawley rats, 3-6 rats per treatment dose, were pretreated with pentobarbital 20 minutes before iv injection of vehicle/peptide or peptide plus stimulator. Injection was made as a 0.1 ml solution. For the non-pentobarbital treated rat assay, peptides were administered iv into the tail vein of conscious rats. All animals were sacrificed by guillotine after iv peptide or vehicle. Trunk blood was collected at +10-15 minutes after decapitation, allowed to clot, centrifuged and serum stored until assayed for GH levels by RIA. The GH RIA reagents were distributed by the NIH. Control data was collected from rats treated with only the corresponding vehicle in the absence of peptide or stimulator. Control stimulated data was collected from rats treated with stimulator alone in the absence of any peptide.

Results

The data obtained show that ghrelin receptor antagonists of the present invention such as HisDβNalDLysTrpD-PheLysNH$_2$, can be used as a tool to disrupt the activity of ghrelin at the level of the CNS. This peptide is a GHRP derivative antagonist. ICV administration of 5 µg of this antagonist prior to i.c.v. injection of ghrelin (500 ng) in free moving, adult rats virtually obliterated the GH response to ghrelin. A similar block of ghrelin (5 µg iv) induced GH release was observed when rats were pretreated peripherally with the GHS-R antagonist (250 µg i.v.). In contrast, this GHS-R antagonist did not significantly reduce the GH response to GHRH (5 µg i.v.). With respect to feeding, i.c.v. administered GHS antagonist (5 µg) significantly inhibited ghrelin's (500 ng i.c.v.) stimulatory effects on food intake in the first hr after injections. These results provide evidence of a modulatory role for endogenous ghrelin in maintaining the high amplitude of spontaneous GH pulses under physiological conditions, likely acting through the GHS-R1a on GHRH containing neurons in the arcuate nucleus (16, 17). While ghrelin may be necessary for the full response of GHRH (the major driving regulator) on pulsatile GH release, it is not an active player in generating the ultradian rhythm of GH secretion. The lack of a dissociated effect on GH and food intake by the GHS antagonist suggest that the GHS-R1a mediates the effects of ghrelin on feeding (via NPY-containing neurons) as well as on GH.

All patents and other publications identified throughout the specification and examples and in the references section are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

REFERENCES

1. Kojima M, Hosada H, Date Y, Nakazato M, Matsuo H, Kangawa K. Ghrelin is a growth-hormone-releasing acylated peptide from stomach. Nature 1999; 402:656-60.
2. Bowers C Y. Growth Hormone Releasing Peptides (GHRPs). In: Handbook of Physiology, Eds. J Kostyo, H Goodman 1999; Oxford University Press, New York, pg 267-297.
3. Bowers C Y. Unnatural growth hormone-releasing peptide begets natural ghrelin. J Clin Endocrinol Metab 2001; 86:1464-1469.
4. Wren A M, Seal L J, Cohen M A, Brynes A E, Frost G S, Murphy K G et al. Ghrelin enhances appetite and increases food intake in humans. J Clin Endocrinol Metab 2001; 86:5992-5995.
5. Laferrere B, Abraham C, Russell C D, Bowers C Y. Growth hormone releasing peptide-2 (GHRP-2), like ghrelin, increases food intake in healthy men. J Clin Endocrinol Metab 2005; 90:611-614.
6. Laferrere B, Hart A B, Bowers C Y. Obese subjects respond to the stimulatory effect of the ghrelin agonist Growth Hormone Releasing Peptide-2 (GHRP-2) on food intake. Obesity 14(6):1056-63, 2006.
7. Bowers C Y. Octanoyl ghrelin is hypothalamic rooted. Endocrinology 146:2508-9, 2005.
8. Sethumadhaven K, Veeraragavan K, Bowers C Y. Demonstration and characterization of the specific binding of growth hormone-releasing peptide (GHRP) to rat anterior pituitary and hypothalamic membranes. Biochem Biophy Res Comm 178(1):31-37, 1991.
9. Bitar K G, Bowers C Y, Coy D H. Effects of Substance P/Bombesin antagonists on the release of growth hormone by GHRP and GHRH. Biochem Biophy Res Comm 180 (1): 156-161, 1991.
10. Veeraragavan K, Sethumadhavan K, Bowers C Y. Growth hormone releasing peptide (GHRP) binding to porcine anterior pituitary and hypothalamic membranes. Life Sciences 50:1149-1155, 1992
11. Camina J P. Cell biology of the ghrelin receptor. J Neuroendocrinol 2006; 18:65-76.
12. Bodart V, Febbraio M, Demers A, McNicoll N, Pohankova P, Perreault A et al. CD36 mediates cardiovascular action of growth hormone-releasing peptides in the heart. Circ Res 2002; 90:844-49.
13. Hoist B, Cygankiewicz A, Jensen T H, Ankersen M, Schwartz T W. High constitutive signaling of the ghrelin receptor-identification of a potent inverse agonist. Mol Endocrinol 2003; 17 (11):2201-10.
14. Hoist B, Holliday N D, Bach A, Elling C E, Cox H M, Schwartz T W. Common structural basis for constitutive activity of the ghrelin receptor family. J Biol Chem 2004; 279:53805-53817.
15. Petersen P S, Wolsbye D, Lang M, Beck-Sickinger A, Schwartz T W, Hoist B. Effect of icv infusion of the ghrelin receptor selective inverse agonist [DArg$^1$, DPhe$^5$, DTrp$^{7,9}$ Leu$^{11}$]-Sub P on body weight gain in rats. Keystone Symposium Gut Hormone and Other Regulators of Appetite, Satiety and Energy Expenditure Mar. 2-7, 2006, p. 53.
16. Hoist B, Mokrosinski J, Lang M, Brandt E, Nygaard R, Frimurer T M, Beck-Sickinger A G, Schwartz T W. Identification of an efficacy switch region in the ghrelin receptor responsible for interchange between agonism and inverse agonism. Journal Biol Chem doi/10.1074, 2007.

17. Zigman J M, Jones J E, Lee C E, Saper C B, Elmquist J K. Expression of ghrelin receptor mRNA in the rat and the mouse brain. J Comparative Neurology 2006; 494:528-548.
18. Zigman K M, Nakano Y, Coppari R, Balthasar N, Marcus J N, Lee C E et al. Mice lacking ghrelin receptors resist the development of diet induced obesity. J Clin Invest 2005; 115:3564-3572.
19. Wortley K E, del Rincon J P, Murray J D, Garcia J, Iida K, Thorner M O, Sleeman M W. Absence of ghrelin protects against early-onset obesity. J Clin Invest 2005; 115:3573-3578.
20. Gelling R W, Overduin J, Morrison C D, Morton G J, Frayo R S, Cummings D E, Schwartz M W. Effect of uncontrolled diabetes on plasma ghrelin concentrations and ghrelin-induced feeding. Endocrinology 2004; 145: 4575-4582.
21. Tannenbaum G S, Epelbaum J, Bowers C Y. Interrelationship between the novel peptide ghrelin and somatostatin/GHRH in regulation of pulsatile growth hormone secretion. Endocrinology 2003; 144:967-974.
22. Tannenbaum G S, Epelbaum J, Bowers C Y. Ghrelin and growth hormone neuroendocrine axis. In: Brain Somatic Cross-Talk and the Central Control of Metabolism. Eds. C Kordon et al. 2003; Springer-Verlag, Berlin/Heidelberg pg 65-80.
23. Bowers C Y, Chang, J-K, Wu S, Linse K D, Hurley D L, Veldhuis J D. Biochemistry of growth hormone secretagogue molecules, In: Fat Loss, Wasting and Cachexia in Medicine, (Ed) Schuster M and Mantovani G, Springer Verlag, Chapter 5.7, p 219-234, 2006.
24. Bowers C Y, Laferrere B, Hurley D L, Veldhuis J D. The role of GHS/Ghrelin in Feeding and Body Composition. Obesity and Energy Metabolism: research and Clinical Applications (Eds) Conn P M and Donohoue P. The Humans Press, 2007.
25. Inui A, Asakawa A, Bowers C Y, Montovani G, Laviano A, Meguid M, Fujimiya M. Ghrelin, appetite and growth—The emerging role of the stomach as an endocrine organ. FASEB Journal 2004; 18:439-456.
26. Van der Lely A J, Tschop M, Heiman M L, Ghigo E. Biological, physiological, pathophysiological and pharmacological aspects of ghrelin. Endocrine Reviews 2004; 25:426-457.
27. Korbonits M, Goldstone A P, Gueorguiev M, Grossman A B. Ghrelin-a hormone with multiple functions. Neuroendocrinology 2004; 25:27-68.

What is claimed:
1. A compound having a formula:

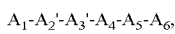

wherein $A_1$ is His, Tyr, desamino Tyr, DAla, β-Ala, CyclohexylAla (Cyclohexylalanine), DArg, Ava (aminovaleric acid), Gly, <Glu (pyroglutamic acid), αAib (alpha-aminoisobutyric acid), γAbu (gamma-aminobutyric acid), αAbu (alpha-aminobutyric acid), α,γAbu (alpha, gamma-diaminobutyric acid or 2,4-diaminobutyric acid), DVal, DPhe, DThr, DPal (pyridylalanine), DLys, AcDLys, DLeu, DTrp, Dβnaphthylalanine or AcDβ-naphthylalanine, wherein the $A_1$ residue is with or without methylation of the terminal nitrogen of the α carbon atom of the $A_1$ residue when a terminal nitrogen is present at the α carbon atom, and wherein the peptide bond between the $A_1$ and $A_2'$ residues is a normal or reduced psi (Ψ, $CH_2NH$) peptide bond;

$A_2'$ is Dα or Dβnaphthylalanine, Trp, D or L Phe, Ala, His, PicLys, DCyclohexylalanine, D-4-halo-Phe or D-4-pyrolidylalanine, wherein $A_2'$ is with or without methylation of the terminal nitrogen of the α carbon atom of the $A_2'$ residue;

$A_3'$ is D or L Lys, lysine derivatives, Orn, Phe, Trp, Leu, Pro, Ser, Pal, or α,γAbu;

$A_4$ is D or L Trp, Phe, Ala, Ser, Tyr, Met, Pro, Thr, ILys, or CyclohexylAla;

$A_5$ is D or L Trp, D or LPhe, Ala, Lys, Arg, Orn, Thr, Leu, or DCyclohexylAla; and $A_6$ is Lys, Arg, Orn, D or L Phe, Pro, Nle (norleucine), or α,γAbu; or prodrugs or pharmaceutically acceptable salts thereof, wherein the $A_6$ residue can be present either in a C terminal amidated form or as a free carboxylic acid.

2. A method for treatment, prevention or management of obesity in an individual, said method comprising the step of administering an effective amount of a compound of claim 1.

3. A method for treatment, prevention or management of diabetes mellitus in an individual in need thereof, said method comprising the step of administering an effective amount of a compound of claim 1.

4. The method of claim 2 further comprising the step of administering at least one other anti-obesity treatment.

5. The method of claim 4, wherein the other anti-obesity treatment is a combination of dietary restriction therapy with a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, leptin, a leptin derivative, an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, or a lipase drug inhibitor administered simultaneously, concurrently or sequentially.

6. A compound having a formula:

wherein $A_1$ is His, Tyr, desamino Tyr, DAla, β-Ala, CyclohexylAla (Cyclohexylalanine), DArg, Ava (aminovaleric acid), Gly, <Glu (pyroglutamic acid), αAib (alpha-aminoisobutyric acid), γAbu (gamma-aminobutyric acid), αAbu (alpha-aminobutyric acid), α,γAbu (alpha, gamma-diaminobutyric acid or 2,4-diaminobutyric acid), DVal, DPhe, DThr, DPal (pyridylalanine), DLys, AcDLys, DLeu, DTrp, Dβnaphthylalanine, or AcDβ-naphthylalanine, wherein the $A_1$ residue is with or without methylation of the terminal nitrogen of the α carbon atom of the $A_1$ residue when a terminal nitrogen is present at the α carbon atom, and wherein the peptide bond between the $A_1$ and $A_2^*$ residues is a normal or reduced psi (Ψ, $CH_2NH$) peptide bond;

$A_2^*$ is Dα or Dβnaphthylalanine, Trp, DPhe, Ala, His, PicLys, DCyclohexylalanine, D-4-halo-Phe or D-4-pyrolidylalanine, wherein the $A_2^*$ is with or without methylation of the terminal nitrogen of the α carbon atom of the $A_2^*$ residue;

$A_3$ is D or L Lys, lysine derivatives, Arg, arginine derivatives, Orn, Phe, Trp, Leu, Pro, Ser, Pal, or α,γAbu;

$A_4$ is D or L Trp, Phe, Ala, Ser, Tyr, Met, Pro, Thr, ILys, or CyclohexylAla;

$A_5$ is D or L Trp, D or L Phe, Ala, Lys, Arg, Orn, Thr, Leu, or DCyclohexylAla; and A₆ is Lys, Arg, Orn, D or L Phe, Pro, Nle (norleucine), or α,γAbu; or prodrugs or pharmaceutically acceptable salts thereof, wherein the A₆ residue can be present either in a C terminal amidated form or as a free carboxylic acid.

7. The compound of claim 1, wherein
$A_1$ is His, D Ala, Tyr, desamino Tyr, Gly, αAib, γAbu or α,γAbu, wherein the $A_1$ residue is with or without methylation of the terminal nitrogen of the α carbon atom of the $A_1$ residue when a terminal nitrogen is present at the α carbon atom, and wherein the peptide bond between the $A_1$ and $A_2'$ residues is a normal or reduced psi (Ψ, CH₂NH) peptide bond;
$A_2'$ is Dα or Dβnaphthylalanine, Trp, DPhe, DCyclohexylalanine, D-4-halo-Phe or D-4-pyrolidylalanine;
$A_{3'}$ is D or L Lys, Orn, Ser, or α,γAbu;
$A_4$ is D or L Trp, Phe, or CyclohexylAla;
$A_5$ is D or L Phe, DTrp, or DCyclohexylAla; and
$A_6$ is Lys, Arg, Orn, or α,γAbu; or prodrugs or pharmaceutically acceptable salts thereof, wherein the $A_6$ residue can be present either in a C terminal amidated form or as a free carboxylic acid.

8. The compound of claim 7, wherein the compound has the formula: Glyψ[CH₂NH]-DβNal-DLys-Trp-DPhe-Lys-NH₂, DAla-DβNal-DLys-DTrp-Phe-Lys-NH₂ or His-Dβ-Nal-DLys-Trp-DPhe-Lys-NH₂.

9. The method of claim 3, wherein the compound has the formula: Glyψ[CH₂NH]-DβNal-DLys-Trp-DPhe-Lys-NH₂, DAla-DβNal-DLys-DTrp-Phe-Lys-NH₂, or His-DβNal-DLys-Trp-DPhe-Lys-NH₂.

10. A compound with the formula: O-(2-methylallyl)benzophenone oxime or methyl 3-(p-tolylcarbamoyl)-2-naphthoate.

\* \* \* \* \*

UNITED STATES PATENT AND TRADEMARK OFFICE
CERTIFICATE OF CORRECTION

PATENT NO. : 8,536,120 B2  
APPLICATION NO. : 12/298826  
DATED : September 17, 2013  
INVENTOR(S) : Bowers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 585 days.

Signed and Sealed this

Fifteenth Day of September, 2015

Michelle K. Lee
*Director of the United States Patent and Trademark Office*

UNITED STATES PATENT AND TRADEMARK OFFICE
CERTIFICATE OF CORRECTION

PATENT NO.        : 8,536,120 B2
APPLICATION NO.   : 12/298826
DATED             : September 17, 2013
INVENTOR(S)       : Cyril Y. Bowers et al.

It is certified that error appears in the above-identified patent and that said Letters Patent is hereby corrected as shown below:

On the title page item 73, should read

Assignee The Administrators of The Tulane Educational Fund,
New Orleans, LA (US)

McGill University,
Montreal (CA)

Signed and Sealed this
Ninth Day of February, 2016

Michelle K. Lee
*Director of the United States Patent and Trademark Office*